US012264202B2

(12) United States Patent
Vikstrom et al.

(10) Patent No.: US 12,264,202 B2
(45) Date of Patent: Apr. 1, 2025

(54) METHODS OF REDUCING OR HINDERING DEVELOPMENT OF ISCHEMIA-REPERFUSION INJURY DUE TO KIDNEY TRANSPLANTATION WITH AN ANTIBODY THAT INHIBITS GRANULOCYTE-COLONY STIMULATING FACTOR (G-CSF) SIGNALING

(71) Applicant: CSL Limited, Melbourne (AU)

(72) Inventors: Ingela Vikstrom, Melbourne (AU); Adriana Baz Morelli, Melbourne (AU); Martin Pearse, Melbourne (AU)

(73) Assignee: CSL LIMITED, Melbourne (AU)

( * ) Notice: Subject to any disclaimer, the term of this patent is extended or adjusted under 35 U.S.C. 154(b) by 0 days.

(21) Appl. No.: 18/152,439

(22) Filed: Jan. 10, 2023

(65) Prior Publication Data
US 2023/0279129 A1 Sep. 7, 2023

Related U.S. Application Data

(63) Continuation of application No. 16/768,159, filed as application No. PCT/AU2018/051272 on Nov. 29, 2018, now abandoned.

(30) Foreign Application Priority Data

Nov. 29, 2017 (AU) ................. 2017904822

(51) Int. Cl.
| | |
|---|---|
| *A61K 39/395* | (2006.01) |
| *A61P 9/10* | (2006.01) |
| *A61P 13/12* | (2006.01) |
| *C07K 16/28* | (2006.01) |
| *A61K 39/00* | (2006.01) |

(52) U.S. Cl.
CPC ............ *C07K 16/2866* (2013.01); *A61P 9/10* (2018.01); *A61P 13/12* (2018.01); *A61K 2039/505* (2013.01); *A61K 2039/545* (2013.01); *C07K 2317/21* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. | |
| 4,676,980 A | 6/1987 | Segal et al. | |
| 4,816,567 A | 3/1989 | Cabilly et al. | |
| 5,225,539 A | 7/1993 | Winter | |
| 5,270,163 A | 12/1993 | Gold et al. | |
| 5,422,248 A | 6/1995 | Smith et al. | |
| 5,475,096 A | 12/1995 | Gold et al. | |
| 5,530,101 A | 6/1996 | Queen et al. | |
| 5,585,089 A | 12/1996 | Queen et al. | |
| 5,589,456 A | 12/1996 | Smith et al. | |
| 5,731,168 A | 3/1998 | Carter et al. | |
| 5,807,715 A | 9/1998 | Morrison et al. | |
| 5,885,793 A | 3/1999 | Griffiths et al. | |
| 6,248,516 B1 | 6/2001 | Winter et al. | |
| 6,300,064 B1 | 10/2001 | Knappik et al. | |
| 7,083,784 B2 | 8/2006 | Dall | |
| 7,108,852 B2 | 9/2006 | Devalaraja et al. | |
| 7,220,407 B2* | 5/2007 | Mehta .................. | A61K 38/193 514/16.4 |
| 7,250,297 B1 | 7/2007 | Beste et al. | |
| 7,618,938 B2* | 11/2009 | Li .......................... | A61P 25/28 530/397 |
| 7,871,979 B2 | 1/2011 | Yorke-Smith et al. | |
| 8,455,435 B2* | 6/2013 | Franz .................. | A61K 31/519 514/7.9 |
| 9,193,793 B2 | 11/2015 | Nash et al. | |
| 9,382,538 B2 | 7/2016 | Collard et al. | |
| 9,649,356 B2 | 5/2017 | Seelen | |
| 2004/0132028 A1 | 7/2004 | Stumpp et al. | |
| 2007/0059280 A1 | 3/2007 | Devalaraja et al. | |
| 2007/0135620 A1 | 6/2007 | Chamberlain et al. | |
| 2007/0224633 A1 | 9/2007 | Skerra et al. | |
| 2008/0139791 A1 | 6/2008 | Lipovsek et al. | |
| 2008/0199426 A1 | 8/2008 | Sukhatme et al. | |
| 2009/0324591 A1 | 12/2009 | Crump et al. | |
| 2010/0004167 A1 | 1/2010 | Yorke-Smith et al. | |

(Continued)

FOREIGN PATENT DOCUMENTS

| | | |
|---|---|---|
| CN | 107106681 A | 8/2017 |
| CN | 109310884 A | 2/2019 |

(Continued)

OTHER PUBLICATIONS

Aggarwal, A. et al., "G-CSF and IL-8 but not GM-CSF correlate with severity of pulmonary neutrophilia in acute respiratory distress syndrome", Eur Respir J., 2000, pp. 895-901, vol. 15, No. 5.
Anzctr, "Trial Review", 2016, pp. 1-6.
Ashchyan, H. et al., "Neutrophilic dermatoses: Pyoderma gangrenosum and other bowel- and arthritis-associated neutrophilic dermatoses", J Am Acad Dermatol, 2018, pp. 1009-1022.
Bendele, A., "Animal models of rheumatoid arthritis", J Musculoskelet Neuronal Interact, 2001, pp. 377-385, vol. 1, No. 4.
Bidyasar, S. et al., "Sweet syndrome associated with granulocyte colony-stimulating factor", J Clin Oncol, 2008, pp. 4355-4356, vol. 26, No. 26.
Bozinovski, S. et al., "Granulocyte/macrophage-colony-stimulating factor (GM-CSF) regulates lung innate immunity to lipopolysaccharide through Akt/Erk activation of NFkappa B and AP-1 in vivo", J Biol Chem, 2002, pp. 42808-42814, vol. 277, No. 45.

(Continued)

*Primary Examiner* — Christine J Saoud
(74) *Attorney, Agent, or Firm* — Scully, Scott, Murphy & Presser, P.C.

(57) ABSTRACT

The present disclosure relates to a method for reducing or hindering development of renal ischemia-reperfusion injury in a subject the method comprising administering an antibody that inhibits granulocyte colony stimulating factor (G-CSF) signaling. In some examples, the ischemia-reperfusion injury is due to or associated with tissue or organ transplantation.

11 Claims, 16 Drawing Sheets

Specification includes a Sequence Listing.

(56) References Cited

U.S. PATENT DOCUMENTS

| | | |
|---|---|---|
| 2011/0110934 A1 | 5/2011 | Wicks et al. |
| 2012/0321630 A1 | 12/2012 | Nash et al. |
| 2013/0259824 A1 | 10/2013 | Wu et al. |
| 2019/0343918 A1 | 11/2019 | Graham et al. |

FOREIGN PATENT DOCUMENTS

| | | |
|---|---|---|
| EP | 0569141 A2 | 11/1993 |
| EP | 1167390 A1 | 1/2002 |
| EP | 1641818 B1 | 12/2008 |
| WO | 1994004678 A1 | 3/1994 |
| WO | 1994007921 A1 | 4/1994 |
| WO | 1995021867 A1 | 8/1995 |
| WO | 1997049805 A2 | 12/1997 |
| WO | 1998044001 A1 | 10/1998 |
| WO | 1999032619 A1 | 7/1999 |
| WO | 1999045110 A1 | 9/1999 |
| WO | 1999049029 A1 | 9/1999 |
| WO | 1999053050 A1 | 10/1999 |
| WO | 1999057134 A1 | 11/1999 |
| WO | 2000034317 A2 | 6/2000 |
| WO | 2001034815 A1 | 5/2001 |
| WO | 2002080967 A1 | 10/2002 |
| WO | 2002088171 A2 | 11/2002 |
| WO | 2002098216 A1 | 12/2002 |
| WO | 2004064724 A2 | 8/2004 |
| WO | 2004108158 A1 | 12/2004 |
| WO | 2005056764 A2 | 6/2005 |
| WO | 2005118629 A1 | 12/2005 |
| WO | 2006033386 A1 | 3/2006 |
| WO | 2007/025166 A2 | 3/2007 |
| WO | 2008003763 A1 | 1/2008 |
| WO | 2008/017126 A1 | 2/2008 |
| WO | 2009/039337 A2 | 3/2009 |
| WO | 2010080538 A1 | 7/2010 |
| WO | 2010085682 A2 | 7/2010 |
| WO | 2011032204 A1 | 3/2011 |
| WO | 2011051489 A2 | 5/2011 |
| WO | 2011103076 A1 | 8/2011 |
| WO | 2011107595 A1 | 9/2011 |
| WO | 2012112188 A1 | 8/2012 |
| WO | 2012/171057 A1 | 12/2012 |
| WO | 2013075066 A2 | 5/2013 |
| WO | 2014072481 A1 | 5/2014 |
| WO | 2014179657 A1 | 11/2014 |
| WO | 2015063611 A2 | 5/2015 |
| WO | 2015127405 A2 | 8/2015 |
| WO | 2019104385 A1 | 6/2019 |
| WO | 2019124666 A2 | 6/2019 |
| WO | 2019178645 A1 | 9/2019 |
| WO | 2020097139 A1 | 5/2020 |
| WO | 2020113270 A1 | 6/2020 |
| WO | 2020248024 A1 | 12/2020 |

OTHER PUBLICATIONS

Butler, D. et al., "What do autoinflammatory syndromes teach about common cutaneous diseases such as pyoderma gangrenosum? A commentary", Dermatol Clin, 2013; pp. 427-435, vol. 31, No. 3.
Cugno, M. et al., "Inflammatory Joint Disorders and Neutrophilic Dermatoses: a Comprehensive Review", Clin Rev Allergy Immunol, 2018, pp. 269-281, vol. 54, No. 2.
De La Lastra, J.M. et al., "Epitope mapping of 10 monoclonal antibodies against the pig analogue of human membrane cofactor protein (MCP)", Immunology, 1999, pp. 663-670, vol. 96, No. 4.
De Vries, B. et al. "Complement factor C5a mediates renal ischemia-reperfusion injury independent from neutrophils", J Immunol., 2003, pp. 3883-3889, vol. 170, No. 7.
Debruin, C. et al., "Most purported antibodies to the human granulocyte colony-stimulating factor receptor are not specific", Exp Hematol, 2010, pp. 1022-1035, vol. 38, No. 11.

Dondelinger, M. et al., "Understanding the Significance and Implications of Antibody Numbering and Antigen-Binding Surface/Residue Definition", Frontiers in Immunology, 2018, pp. 1-14, vol. 9.
Draper, B. et al., "Bullous Sweet's syndrome in congenital neutropenia: association with pegfilgrastim", J Am Acad Dermatol, 2005, pp. 901-905, vol. 52, No. 5.
Elsasser, A. et al., "The fusion protein AML1-ETO in acute myeloid leukemia with translocation t(8;21) induces c-jun protein expression via the proximal AP-1 site of the c-jun promoter in an indirect, JNK-dependent manner", Oncogene, 2003, pp. 5646-5657, vol. 22, No. 36.
Fujii, A. et al., "Sweet's Syndrome Successfully Treated with Granulocyte and Monocyte Adsorption Apheresis", Case Rep Dermatol., 2017, pp. 13-18, vol. 9, No. 2.
Fukunaga, R. et al., "Three different mRNAs encoding human granulocyte colony-stimulating factor receptor", Proc Natl Acad Sci USA, 1990, pp. 8702-8706, vol. 87, No. 22.
Goldberg, G. et al., "G-CSF and Neutrophils are Nonredundant Mediators of Murine Experimental Autoimmune Uveoretinitis", Am J Pathol, 2016, pp. 172-184, vol. 186, No. 1.
Guo, Y. et al., "The origin, transmission and clinical therapies on coronavirus disease 2019 (COVID-19) outbreak—an update on the status", Mil Med Res, 2020, pp. 1-10, vol. 7, No. 1.
Huang, C. et al., "Clinical features of patients infected with 2019 novel coronavirus in Wuhan, China", Lancet, 2020, pp. 497-506, vol. 395.
Kawakami, T. et al., "Elevated serum granulocyte colony-stimulating factor levels in patients with active phase of sweet syndrome and patients with active behcet disease: implication in neutrophil apoptosis dysfunction", Arch Dermatol, 2004, pp. 570-574, vol. 140, No. 5.
Ko, B. et al., "Affinity Maturation of Monoclonal Antibody 1E11 by Targeted Randomization in CDR3 Regions Optimizes Therapeutic Antibody Targeting of HER2-Positive Gastric Cancer", PLoS One, 2015, pp. 1-16, vol. 10, No. 7.
Layton, J. et al., "Identification of a ligand-binding site on the granulocyte colony-stimulating factor receptor by molecular modeling and mutagenesis", J Biol Chem., 1997, pp. 29735-29741, vol. 272, No. 47.
Layton, J. et al., "Neutralising antibodies to the granulocyte colony-stimulating factor receptor recognise both the Immunoglobulin-like domain and the cytokine receptor homologous domain", Growth Factors, 1997, pp. 117-130, vol. 14.
Layton, J. et al., "Interaction of granulocyte colony-stimulating factor (G-CSF) with its receptor. Evidence that Glu19 of G-CSF interacts with Arg288 of the receptor", J Biol Chem., 1999; pp. 17445-17451, vol. 274, No. 25.
Layton, J. et al., "Identification of ligand-binding site III on the immunoglobulin-like domain of the granulocyte colony-stimulating factor receptor", J Biol Chem., 2001, pp. 36779-36787, vol. 276, No. 39.
Layton, J. et al., "The interaction of G-CSF with its receptor", Front Biosci., 2006, pp. 3181-3189, vol. 11.
Lescure, F. et al., "Clinical and virological data of the first cases of COVID-19 in Europe: a case series", Lancet Infect Dis., 2020, pp. 697-706, vol. 20, No. 6.
Li, Y. et al., "X-ray snapshots of the maturation of an antibody response to a protein antigen", Nat Struct Biol., 2003, pp. 482-488, vol. 10, No. 6.
Liao, J. et al., "Progress on role of cytokine storm in exacerbation of coronavirus disease 2019 (COVID-19): Review", Chinese Journal of Cellular and Molecular Immunology, 2020, pp. 941-947, vol. 36, No. 10.
Lloyd, C. et al., "Modelling the human immune response: performance of a 1011 human antibody repertoire against a broad panel of therapeutically relevant antigens", Protein Eng Des Sel., 2009, pp. 159-168, vol. 22, No. 3.
Navarini, A. et al., "Neutrophilic dermatoses and autoinflammatory diseases with skin involvement-innate immune disorders", Semin Immunopathol, 2016, pp. 45-56, vol. 38, No. 1.
Nelson, C., "Neutrophilic dermatoses: Pathogenesis, Sweet syndrome, neutrophilic eccrine hidradenitis, and Behçet disease", J Am Acad Dermatol., 2018, pp. 987-1006, vol. 79, No. 6.

(56) References Cited

OTHER PUBLICATIONS

Nogueira, B. et al., "Granulocyte colony stimulating factor prevents kidney infarction and attenuates renovascular hypertension", Cell Physiol Biochem, 2012, pp. 143-152, vol. 29.
Prendiville, J. et al., "Neutrophilic dermatoses in two children with idiopathic neutropenia: association with granulocyte colony-stimulating factor (G-CSF) therapy", Pediatr Dermatol., 2001, pp. 417-421, vol. 18, No. 5.
Qin, C. et al., "Dysregulation of Immune Response in Patients With Coronavirus 2019 (COVID-19) in Wuhan, China", Clin Infect Dis., 2020, pp. 762-768, vol. 71, No. 15.
Queto, T. et al., "G-CSF suppresses allergic pulmonary inflammation, downmodulating cytokine, chemokine and eosinophil production", Life Sci., 2011, pp. 830-838, vol. 88.
Rajpal, A. et al., A general method for greatly improving the affinity of antibodies by using combinatorial libraries, Proc Natl Acad Sci, 2005, pp. 8466-8471, vol. 102, No. 24.
Scalzo-Inguanti K. et al., "A neutralizing anti-G-CSFR antibody blocks G-CSF-induced neutrophilia without inducing neutropenia in nonhuman primates", J Leukoc Biol., 2017, pp. 537-549, vol. 102, No. 2.
Steinberg, K. et al., Evolution of bronchoalveolar cell populations in the adult respiratory distress syndrome, Am J Respir Crit Care Med., 1994, pp. 113-122, vol. 150, No. 1.
Tian, S. et al., "Pulmonary Pathology of Early-Phase 2019 Novel Coronavirus (COVID-19) Pneumonia in Two Patients With Lung Cancer", J Thorac Oncol., 2020, pp. 700-704, vol. 15, No. 5.
Toussaint, M. et al. "Host DNA released by NETosis promotes rhinovirus-induced type-2 allergic asthma exacerbation", Nat Med., 2017, pp. 681-691, vol. 23, No. 6.
Uhara, H. et al., "Neutrophilic dermatoses with acute myeloid leukemia associated with an increase of serum colony-stimulating factor", J Am Acad Dermatol., 2008, pp. S10-S12.
Wang, H. et al. "Anti G-CSFR Antibody Treatment Suppresses Neutrophilic and Type-2 Lung Inflammation in an Allergic Asthma Model Worsened by Neonatal Co-Infection", Respirology, 2018, pp. 26, vol. 23. 111 River ST, Hoboken 07030-5774, NJ USA: Wiley, 2018.
Wang, H. et al. "G-CSFR antagonism reduces neutrophilic inflammation during pneumococcal and influenza respiratory infections without compromising clearance", Sci Rep., 2019, pp. 1-12.
Yao, X. et al., "The A's Have It: Developing Apolipoprotein A-I Mimetic Peptides Into a Novel Treatment for Asthma", Chest, 2016, pp. 283-288, vol. 150, No. 2.
Zhang, Y. et al., "Ischemia-reperfusion induces G-CSF gene expression by renal medullary thick ascending limb cells in vivo and in vitro", Am J Physiol Renal Physiol., 2004, pp. F1193-F1201, vol. 286, No. 6.
Higuchi, T. et al., "Granulocyte Colony-Stimulating Factor Prevents Reperfusion Injury After Heart Preservation", Ann Thorac Surg., Apr. 2008, pp. 1367-1373, vol. 85, No. 4.
Jiang, H. et al., "Role for Granulocyte Colony Stimulating Factor in Angiotensin II-Induced Neutrophil Recruitment and Cardiac Fibrosis in Mice", American Journal of Hypertension, 2013, pp. 1224-1233, vol. 26, No. 10.
Campbell, I. et al., "Therapeutic Targeting of the G-CSF Receptor Reduces Neutrophil Trafficking and Joint Inflammation in Antibody-Mediated Inflammatory Arthritis", The Journal of Immunology, 2016, pp. 4392-4401.
Banuelos, J. et al., "Granulocyte Colony-Stimulating Factor Blockade Enables Dexamethasone to Inhibit Lipopolysaccharide-Induced Murine Lung Neutrophils", PLoS One, 2017, pp. 1-16, vol. 12, No. 5.
Salvadori, M. et al., "Update on ischemia-reperfusion injury in kidney transplantation: Pathogenesis and treatment", World Journal of Transplantation, 2015, pp. 52-67, vol. 5, No. 2.
Nishida, M. et al., "How Does G-CSF Act on the Kidney during Acute Tubular Injury", Nephron Exp Nephrol, 2006, pp. e123-e128, vol. 104.
Li, Y. et al., "Pretreatment with granulocyte colony-stimulating factor attenuated renal ischaemia and reperfusion injury via activation of PI3/Akt signal pathway", Nephrology (Carlton), Dec. 2008, pp. 508-516, vol. 13.
Shima, C. et al., "Neuroprotective effects of granulocyte colony-stimulating factor on ischemia-reperfusion injury of the retina", Ophthalmic Res, 2012, pp. 199-207.
Bostanci, M. et al., "The protective effect of G-CSF on experimental ischemia/reperfusion injury in rat ovary", Arch Gynecol Obstet, Apr. 2016, pp. 789-795, vol. 293.
Ueda, K. et al., "Granulocyte colony stimulating factor directly inhibits myocardial ischemia-reperfusion injury through Akt-endothelial NO synthase pathway", Arterioscler Thromb Vasc Biol, Jun. 2006, pp. e108-e113.
Lu, C. et al., "Neuroprotection of G-CSF in cerebral ischemia", Front Biosci, May 2007, pp. 2869-2875.
Akihama, S. et al., "Bone marrow-derived cells mobilized by granulocyte-colony stimulating factor facilitate vascular regeneration in mouse kidney after ischemia/reperfusion injury", Tohoku J Exp Med., Dec. 2007, pp. 341-249.
Yan, J. et al., "Granulocyte Colony-Stimulating Factor Attenuates Renal Ischemia-Reperfusion Injury by Inducing Myeloid-Derived Suppressor Cells", J Am Soc Nephrol, Apr. 2020, pp. 731-746, vol. 31, No. 4.

\* cited by examiner

METHODS OF REDUCING OR HINDERING DEVELOPMENT OF ISCHEMIA-REPERFUSION INJURY DUE TO KIDNEY TRANSPLANTATION WITH AN ANTIBODY THAT INHIBITS GRANULOCYTE-COLONY STIMULATING FACTOR (G-CSF) SIGNALING

RELATED APPLICATION DATA

This application is a continuation of U.S. patent application Ser. No. 16/768,159 filed on May 29, 2020, which claims priority from Australian Patent Application No. 2017904822 filed on 29 Nov. 2017 and entitled "Method of treating or preventing ischemia-reperfusion injury". The entire contents of that application are hereby incorporated by reference.

SEQUENCE LISTING

The Sequence Listing in an XML format, named as 38400Z_SequenceListing.xml of 27,090 bytes, created on Jan. 10, 2023, and submitted to the United States Patent and Trademark Office via EFS-Web, is incorporated herein by reference. No new matter is introduced.

FIELD

The present disclosure relates to methods of treating or preventing ischemia-reperfusion injury in a subject by antagonizing granulocyte-colony stimulating factor (G-CSF) signaling and uses thereof, e.g., in organ transplantation.

BACKGROUND

Ischemia-reperfusion injury (IRI) is a pathological condition caused by ischemia, i.e. a restriction or reduction of the blood supply to a tissue or organ, for example, a deceased donor organ for transplantation, followed by subsequent reperfusion and reoxygenation. Ischemia causes deprivation of oxygen and nutrients to cells and inadequate removal of metabolic waste, and can rapidly lead to necrosis and inflammation. Reperfusion of a tissue or organ after a period of ischemia returns the blood supply and oxygen, however the reperfusion itself can accentuate the oxidation and inflammation caused by the initial ischemia and cause further injury. Reoxygenation can cause oxidative damage to cellular proteins, DNA and the plasma membrane. Such oxidative damage may in turn cause the release of free radicals resulting in further cellular damage. Reperfusion injury is characterized by among other things, the generation of reactive oxygen species, complement activation, cellular inflammation and endothelial cell damage.

In organ transplantation, ischemia-reperfusion injury can be defined as 'warm' IRI or 'cold' IRI. Warm IRI occurs in situ during organ transplantation surgery or during various forms of shock or trauma. Cold IRI occurs during ex vivo preservation and is usually coupled with warm IRI during organ transplantation surgery.

Both the innate and adaptive immune systems have a central role in the pathogenesis of ischemia-reperfusion injury. In terms of innate immunity, danger signals released by dying cells activate Toll-like receptors leading to activation and/or production of cellular and soluble factors that regulate inflammatory cell recruitment and the production of inflammatory mediators, e.g. chemokines, cytokines and free radicals. Neutrophils are among the primary inflammatory cell responders following ischemia and reperfusion. In the inflammatory environment, dendritic cells take up and process antigens from dying cells, migrate to the lymph nodes and activate antigen-specific cells of the adaptive immune system. Thus, the pathogenesis of ischemia-reperfusion injury is complex and tissue damage likely occurs through several mechanisms such as cell death, microvascular dysfunction, transcriptional reprogramming, activation of complement and the innate and adaptive immune systems.

Ischemia-reperfusion injury is a frequent event in transplantation, including kidney transplantation, and is a relevant factor in determining both short-term and long-term graft outcome. In kidney transplantation, IRI affects endothelial cells and tubular epithelial cells and can cause acute kidney injury and delayed graft function (DGF), which can impair graft survival. DGF is one of the more frequent early complications after deceased donor, or expanded-criteria donor kidney transplantation and is primarily caused by tubular epithelial cell necrosis caused by IRI (Schröppel B, et al., *Kidney Int.* 2014).

Compounds that are currently being tested in clinical trials to treat ischemia-reperfusion injury include eculizumab, which is a humanized monoclonal antibody against the C5 component of the complement cascade (Rother R, et al. *Nat Biotechnol.* 2007). Granulocyte-colony stimulating factor (G-CSF) has also been investigated as a therapeutic agent for the treatment of reperfusion injury, see Nogueira et al., *Cell Phys Biochem* (2006) and Li et al., *Nephrology* (2008). These studies have shown that treatment with G-CSF has protective effects in kidney ischemia.

However, effective therapies to prevent or treat ischemia-reperfusion injury have been elusive. It will therefore be clear to the skilled person from the foregoing, that there is a need in the art for strategies and methods to prevent or treat the damage caused by ischemia-reperfusion injury.

SUMMARY

In producing the present invention, the inventors proceeded against prior teachings that G-CSF may have a protective role in ischemia-reperfusion injury and instead studied the effects of inhibiting G-CSF signaling on ischemia-reperfusion injury. The inventors found that by administering a compound that inhibits G-CSF signaling, the effects of ischemia-reperfusion injury were reduced. Additionally, the inventors found that by inhibiting G-CSF signaling they could prevent or treat ischemia-reperfusion injury to a similar degree as inhibiting complement activation at the level of C5. These findings provide the basis for methods for preventing or treating ischemia-reperfusion injury by inhibiting G-CSF signaling.

Accordingly, in an example, the present disclosure provides a method for preventing or treating ischemia-reperfusion injury in a subject, the method comprising administering a compound that inhibits granulocyte colony stimulating factor (G-CSF) signaling.

The present disclosure also provides a compound that inhibits G-CSF signaling for use in the prevention or treatment of ischemia-reperfusion injury.

The present disclosure also provides use of a compound that inhibits G-CSF signaling in the manufacture of a medicament for the prevention or treatment of ischemia-reperfusion injury.

In some examples, the ischemia and/or reperfusion injury is due to or associated with organ transplantation, cold organ storage, brain death, atherosclerosis, thrombosis, thromboembolism, lipid-embolism, trauma, bleeding, a stent, surgery, angioplasty, bypass surgery, total ischemia, myocardial infarction, stroke, peripheral vascular disease, sepsis, a tumor or combinations thereof.

In some examples, the ischemia-reperfusion injury is warm ischemia-reperfusion injury. In some examples, the ischemia-reperfusion injury is cold ischemia-reperfusion injury.

In some examples, the compound that inhibits G-CSF signaling is administered to the subject.

In one example, the ischemia-reperfusion injury is due to or associated with one or more of the following:
  (i) organ transplantation;
  (ii) surgery;
  (iii) trauma;
  (iv) sepsis;
  (v) a tumor; and
  (vi) stroke.

In one example the ischemia-reperfusion injury is due to or associated with surgery. In one example the ischemia-reperfusion injury is due to or associated with coronary artery bypass surgery, e.g., a double bypass (in which two coronary arteries are bypassed (e.g., the left anterior descending coronary artery (LAD) and right coronary artery (RCA)); a triple bypass (in which three vessels are bypassed e.g., LAD, RCA and left circumflex artery (LCX)); a quadruple bypass (in which four vessels are bypassed (e.g., LAD, RCA, LCX and first diagonal artery of the LAD)); or a quintuple bypass (in which five arteries are bypassed).

In one example, the ischemia-reperfusion injury is due to or associated with organ transplantation, e.g., a solid organ transplantation. In one example, the organ transplantation is a kidney transplantation. In one example, the organ transplantation is a liver transplantation. In one example, the organ transplantation is a heart transplantation. In one example, the organ transplantation is a pancreas transplantation. In one example, the organ transplantation is a lung transplantation. In one example, the organ transplantation is a stomach transplantation. In one example, the organ transplantation is an intestine transplantation. In one example, the organ transplantation is a testis transplantation.

In a still further example, the organ transplantation is a skin transplantation, e.g., a full thickness skin transplantation.

In one example, the ischemia-reperfusion injury is due to or associated with a tissue transplantation. In one example, the tissue transplantation is a blood vessel transplantation. In one example, the tissue transplantation is a skin transplantation, for example vascularized skin. In one example, the tissue transplantation is a pancreatic islet transplantation. In one example, the tissue transplantation is a corneal transplantation. In one example, the tissue transplantation is a musculoskeletal transplantation.

When the ischemia-reperfusion injury is due to or associated with transplantation (e.g., organ transplantation), the compound that inhibits G-CSF signaling can be administered before, during and/or after transplantation. In some examples, the compound that inhibits G-CSF signaling is administered to the subject, wherein the subject is a tissue or organ transplantation recipient. In some examples, the compound that inhibits G-CSF signaling is administered to a tissue or organ transplantation donor.

In some examples, the tissue or organ transplantation donor is a living donor. In some examples, the tissue or organ transplantation donor is a deceased donor. In some examples, the tissue or organ transplantation donor is a donation after brain death (DBD) donor. In some examples, the tissue or organ transplantation donor is a donation after circulatory death (DCD) donor. In some examples, the tissue or organ transplantation donor is an expanded-criteria donor (ECD). In some examples, the tissue or organ transplantation donor is a standard-criteria donor (SCD).

In some examples, the compound that inhibits G-CSF signaling is administered to a harvested organ ex vivo, prior to organ transplantation. For example, the harvested organ can be perfused or infused with a solution comprising the compound that inhibits G-CSF signaling prior to transplantation.

The present disclosure also provides a method of tissue or organ transplantation or for improving outcome of a tissue or organ transplantation or improving function of a transplanted tissue or organ or for preventing delayed graft function, the method comprising administering a compound that inhibits G-CSF signaling to a harvested tissue or organ ex vivo and transplanting the harvested tissue or organ into a tissue or organ transplant recipient.

In some examples, the compound that inhibits G-CSF signaling is administered to the organ transplantation donor and/or the organ transplantation recipient and/or the harvested organ. In some examples, the compound that inhibits G-CSF signaling is administered to the organ transplantation donor and the organ transplantation recipient. In some examples, the compound that inhibits G-CSF signaling is administered to the organ transplantation donor and the harvested organ. In some examples, the compound that inhibits G-CSF signaling is administered to the organ transplantation recipient and the harvested organ.

In one example of the disclosure, the compound that inhibits G-CSF signaling is administered before reperfusion, for example, in the case of a transplant (e.g., organ transplant), the compound that inhibits G-CSF signaling is administered to an organ transplant recipient prior to reperfusion of the transplanted organ (e.g., the compound. that inhibits G-CSF signaling is administered prior to the transplantation or during the transplantation but before reperfusion, e.g., before clamps restricting the flow of blood are released).

In some examples, the compound that inhibits G-CSF signaling is administered before ischemia. In one example, the compound that inhibits G-CSF signaling is administered between between 0 days (e.g., immediately prior to either ischemia or reperfusion) to 7 days before ischemia or reperfusion. For example, the compound that inhibits G-CSF signaling is administered between 0 days and 6 days or 5 days or 4 days before reperfusion or ischemia. For example, the compound that inhibits G-CSF signaling is administered between 0 and 72 hours before reperfusion or ischemia. In one example, the compound that inhibits G-CSF signaling is administered between 6 and 48 hours before reperfusion or ischemia. In one example, the compound that inhibits G-CSF signaling is administered between 12 and 36 hours before reperfusion or ischemia. In one example, the compound that inhibits G-CSF signaling is administered about 24 hours before reperfusion or ischemia.

In some examples, the compound that inhibits G-CSF signaling is administered at least 1 hour before reperfusion or ischemia (and up to 7 days before reperfusion or ischemia). In some examples, the compound that inhibits G-CSF signaling is administered at least 2 or at least 4 or at least 6 or at least 8 or at least 10 or at least 12 hours or at least 14 hours or at least 16 hours or at least 18 hours or at least 20 hours or at least 22 hours or at least 24 hours before reperfusion or ischemia. In some examples, the compound that inhibits G-CSF signaling is administered at least 24 hours before reperfusion or ischemia.

When discussing the timing of administration of a compound herein, the discussion shall relate to multiple administrations of the compound. For example, when stating that a compound is administered between 0 days and 7 days before ischemia or reperfusion, the present disclosure encompasses multiple administrations of the compound (e.g., 2 or 3 or 4 or 5 etc.) between 0 days and 7 days before ischemia or reperfusion.

Additionally, in the case of a transplant, the compound can be administered multiple times following transplantation.

When discussing the timing of administration of a compound herein, the disclosure will also be taken to provide explicit support for a single administration of the compound.

It will be apparent to the skilled person from the foregoing, that the present disclosure provides a method of transplantation (e.g., organ transplantation) or for improving outcome of transplantation (e.g., organ transplantation) or improving function of a transplant (e.g., a transplanted organ) or for preventing delayed graft function, the method comprising administering a compound that inhibits G-CSF signaling to a transplant donor prior to collection of tissue or an organ; collecting the transplant (e.g., tissue/organ) and transplanting the tissue or organ into an organ transplant recipient.

The present disclosure also provides a method for preparing a transplant tissue or organ from a tissue or organ donor to improve tissue or organ function in a tissue or organ transplant recipient, the method comprising administering to the tissue or organ donor a compound that inhibits G-CSF signaling prior to collection of the tissue or organ.

The present disclosure additionally provides a method for preventing tissue or organ transplant rejection, the method comprising administering to a tissue or organ donor a compound that inhibits G-CSF signaling prior to collection of the tissue or organ, collecting the tissue or organ and transplanting the tissue or organ into a tissue or organ transplant recipient.

In some examples, the method additionally comprises administering the compound that inhibits G-CSF signaling to the transplant recipient. For example, the compound that inhibits G-CSF signaling is administered to the transplant recipient before the transplant or at or around the time of transplanting the tissue or organ. In another example, the compound that inhibits G-CSF signaling is administered to the transplant recipient during tissue or organ transplantation surgery.

The present disclosure also provides a method of organ transplantation or for improving outcome of a tissue or organ transplantation or improving function of a transplanted tissue or organ or for preventing delayed graft function, the method comprising administering a compound that inhibits G-CSF signaling to a transplant recipient prior to transplanting the tissue or organ and then transplanting the organ into the transplant recipient.

In one example, the organ transplant donor is brain dead. For example, the organ donor is alive and on life support but is brain dead. Additional donors are described herein and taken to apply to this example of the disclosure.

In the case of administration to an organ donor, the compound that inhibits G-CSF signaling can be administered before the organ is collected, e.g., between 0 and 72 hours before organ collection. In one example, the compound that inhibits G-CSF signaling is administered between 6 and 48 hours before organ collection. In one example, the compound that inhibits G-CSF signaling is administered between 12 and 36 hours before organ collection. In one example, the compound that inhibits G-CSF signaling is administered about 24 hours before organ collection.

In the case of administration to a brain dead donor, the compound that inhibits G-CSF signaling can be administered at a time between brain death and organ collection. In some examples, the compound that inhibits G-CSF signaling can be administered is administered within 48 hours of brain death being declared, e.g., within 24 hours or 12 hours or 6 hours of brain death being declared.

In some examples, the compound that inhibits G-CSF signaling is administered as a single dose.

In some examples, the compound that inhibits G-CSF signaling is administered in a plurality of doses. For example, the compound is administered to a transplant recipient prior to transplantation or during transplantation and then one or more additional doses is(are) administered to the recipient following transplantation. In another example, the compound that inhibits G-CSF signaling is administered to a transplant donor or a donated tissue or organ and then one or more additional doses is(are) administered to a transplant recipient following transplantation.

In some examples, the compound that inhibits G-CSF signaling is administered in a prophylactically or therapeutically effective amount. In some examples, the compound that inhibits G-CSF signaling is administered at a dose of between about 0.01 mg/kg to about 50 mg/kg, such as between about 0.05 mg/kg to about 30 mg/kg, for example, between about 0.1 mg/kg to about 20 mg/kg, for example, between about 1 mg/kg to about 10 mg/kg. In some examples, the compound that inhibits G-CSF signaling is administered at a dose of between about 0.1 mg/kg to about 1 mg/kg. In some examples, the compound that inhibits G-CSF signaling is administered at a dose of between about 0.4 mg/kg to about 0.5 mg/kg. In one example, the compound that inhibits G-CSF signaling is administered at a dose of about 0.1 mg/kg. In one example, the compound that inhibits G-CSF signaling is administered at a dose of about 0.2 mg/kg. In one example, the compound that inhibits G-CSF signaling is administered at a dose of about 0.3 mg/kg. In one example, the compound that inhibits G-CSF signaling is administered at a dose of about 0.4 mg/kg. In one example, the compound that inhibits G-CSF signaling is administered at a dose of about 0.5 mg/kg. In one example, the compound that inhibits G-CSF signaling is administered at a dose of about 0.6 mg/kg. In one example, the compound that inhibits G-CSF signaling is administered at a dose of about 0.7 mg/kg. In one example, the compound that inhibits G-CSF signaling is administered at a dose of about 0.8 mg/kg. In one example, the compound that inhibits G-CSF signaling is administered at a dose of about 1 mg/kg. In some examples, the compound that inhibits G-CSF signaling is administered at a dose of between about 2 mg/kg to about 8 mg/kg. In one example, the compound that inhibits G-CSF signaling is administered at a dose of between about 4 mg/kg to about 6 mg/kg. In one example, the compound that inhibits G-CSF signaling is administered at a dose of about 5 mg/kg.

In some examples, the compound that inhibits G-CSF signaling is administered in an amount that causes neutropenia. For example, the compound that inhibits G-CSF signaling is administered in an amount that causes transient neutropenia, e.g., for a period of less than one week or less than 5 days or less than 3 days or less than 1 day.

In some examples, the compound that inhibits G-CSF signaling is administered in an amount that does not cause neutropenia.

In one example, the compound that inhibits G-CSF signaling is administered in an amount sufficient to reduce or prevent inflammation. In one example, the compound that inhibits G-CSF signaling is administered in an amount sufficient to reduce or prevent oxidative damage.

In one example, the compound that inhibits G-CSF signaling is administered in an amount sufficient to have one or more of the following effects:
  (i) reduce or prevent neutrophil infiltration, e.g., into a transplanted organ in the case of an organ transplantation; and
  (ii) reduce or prevent macrophage infiltration, e.g., into a transplanted organ in the case of an organ transplantation.

In one example, the compound that inhibits G-CSF signaling is administered in an amount sufficient to reduce or prevent neutrophil infiltration. In one example, the compound that inhibits G-CSF signaling is administered in an amount sufficient to reduce or prevent macrophage infiltration. In one example, the compound that inhibits G-CSF signaling is administered in an amount sufficient to reduce or inhibit expression of interleukin 8 receptor beta (IL-8Rβ). In one example, the compound that inhibits G-CSF signaling is administered in an amount sufficient to reduce or inhibit expression of monocyte chemoattractant protein 1 (MCP-1).

In one example, the compound that inhibits G-CSF signaling is administered in an amount sufficient to have one or more of the following effects:
  (i) reduce or prevent an increase in serum or plasma creatinine levels; and
  (ii) reduce or prevent an increase in serum or plasma urea levels.

Serum or plasma creatinine levels and serum or plasma urea levels are measures of kidney function and are useful in assessing delayed graft function, e.g., in the case of a kidney transplantation, as described herein.

In one example, the compound that inhibits G-CSF signaling is administered in an amount sufficient to reduce or prevent an increase in serum or plasma creatinine levels. In one example, the compound that inhibits G-CSF signaling is administered in an amount sufficient to reduce or prevent an increase in serum or plasma urea levels.

Increased levels of albumin and/or blood in urine can also indicate impaired kidney function or kidney damage. In one example, the compound that inhibits G-CSF signaling is administered in an amount sufficient to reduce or prevent an increase in urine albumin levels. In one example, the compound that inhibits G-CSF signaling is administered in an amount sufficient to reduce or prevent an increase in levels of blood in the subject's urine.

In one example, the compound that inhibits G-CSF signaling is administered in an amount sufficient to reduce or inhibit expression of one or more of the following, e.g. by cells of the transplanted organ in the case of an organ transplantation:
  (i) kidney injury molecule 1 (KIM-1);
  (ii) neutrophil gelatinase-associated lipocalin (NGAL);
  (iii) interleukin 1 beta (IL-1β);
  (iv) interleukin 6 (IL-6);
  (v) tumor necrosis factor alpha (TNFα);
  (vi) complement component 5a receptor 1 (C5AR1);
  (vii) macrophage inflammatory protein 2-alpha (MIP2-alpha);
  (viii) intercellular Adhesion Molecule 1 (ICAM-1);
  (ix) E-selectin;
  (x) C-X-C motif chemokine ligand 1 (CXCL1);
  (xi) interleukin 8 receptor beta (IL-8Rβ); and
  (xii) monocyte chemoattractant protein 1 (MCP-1).

In some examples, the compound that inhibits G-CSF signaling is administered in an amount sufficient to reduce or prevent complement C5 activation.

In some examples, the compound that inhibits G-CSF signaling is administered in an amount sufficient to reduce or prevent C5b-9 deposition, e.g. on the surface of cells of the transplanted organ in the case of an organ transplantation.

Methods for assessing each of the foregoing are known in the art and/or described herein. Furthermore, a person skilled in the art will appreciate that the term "reduce" is used herein to refer to a lower amount of any of the items listed above, relative to either the amount in the subject prior to administration of the compound that inhibits G-CSF signaling, or relative to the amount in a corresponding control subject.

In one example, the compound that inhibits G-CSF signaling is administered in combination with another compound. In some examples, the other compound is hydrogen sulfide. In some examples, the other compound is an anti-inflammatory compound and/or specifically inhibits or reduces the expression or activity of one or more of the molecules listed at (i)-(x) above. In some examples, the other compound is an immunosuppressant, e.g. cyclosporine. Suitable immunosuppressants will be known in the art and include those described in James & Mannon, Curr Transplant Rep (2015), which is incorporated herein by reference. Alternatively, or additionally, the other compound is a corticosteroid, such as prednisone and/or prednisolone. Alternatively, or additionally, the other compound is methotrexate. Alternatively, or additionally, the other compound is cyclophosphamide. Alternatively, or additionally, the other compound is mycophenolate mofetil. In some examples, the other compound is TRO40303, as described in Le Lamer et al., *J Transl Med* (2014). In some examples, the other compound is superoxide dismutase. In some examples, the other compound is metformin. In some examples, the other compound is a cannabinoid or a synthetic analog thereof. In some examples, the other compound is one that is commonly used in transplantation surgery.

In some examples, the compound that inhibits G-CSF signaling is administered in combination with a cell. In some examples, the cell is a stem cell, such as a mesenchymal stem cell.

In some examples, the compound that inhibits G-CSF signaling is administered in combination with a gene therapy.

In one example, the compound that inhibits G-CSF signaling is administered simultaneously with the other compound. In one example, the compound that inhibits G-CSF signaling is administered before the other compound. In one example, the compound that inhibits G-CSF signaling is administered after the other compound.

In one example, both the compound that inhibits G-CSF signaling and the other compound are administered to an organ transplant recipient. Suitable other compounds are described above.

In one example, the compound that inhibits G-CSF signaling is administered to an organ transplant donor prior to collection of an organ for transplant and the other compound is administered to the organ transplant recipient, optionally in combination with the compound that inhibits G-CSF signaling. Suitable other compounds are described above.

In one example, the compound that inhibits G-CSF signaling binds to G-CSF or to G-CSF receptor (G-CSFR). In one example, the compound that inhibits G-CSF signaling binds to G-CSF. In one example, the compound that inhibits G-CSF signaling binds to G-CSF receptor (G-CSFR).

In one example, the compound that inhibits G-CSF signaling is a protein.

In one example, the compound that inhibits G-CSF signaling is a protein comprising an antibody variable region that binds to or specifically binds to G-CSFR and neutralizes G-CSF signaling. Reference herein to a protein or antibody that "binds to" G-CSFR provides literal support for a protein or antibody that "binds specifically to" G-CSFR.

In one example, the compound that inhibits G-CSF signaling is a protein comprising an antibody variable region that binds to or specifically binds to G-CSF and neutralizes G-CSF signaling. Reference herein to a protein or antibody that "binds to" G-CSF provides literal support for a protein or antibody that "binds specifically to" G-CSF.

In some examples, the compound that inhibits G-CSF signaling is a protein comprising a Fv. In some examples, the protein is selected from the group consisting of:
  (i) a single chain Fv fragment (scFv);
  (ii) a dimeric scFv (di-scFv); or
  (iv) a diabody;
  (v) a triabody;
  (vi) a tetrabody;
  (vii) a Fab;
  (viii) a F(ab')$_2$;
  (ix) a Fv;
  (x) one of (i) to (ix) linked to a constant region of an antibody, Fc or a heavy chain constant domain ($C_H$) 2 and/or $C_H$3;
  (xi) one of (i) to (ix) linked to albumin, functional fragments or variants thereof or a protein (e.g., antibody or antigen binding fragment thereof) that binds to albumin; or
  (xii) an antibody.

In one example, the protein is an antibody. In one example, the antibody is a naked antibody. Exemplary antibodies are described in WO2012171057, which is incorporated herein by reference.

In one example, the protein is an antibody which binds to hG-CSFR expressed on the surface of a cell at an affinity of at least about 5 nM. In one example, the protein is an antibody which binds to hG-CSFR expressed on the surface of a cell at an affinity of at least about 4 nM. In one example, the protein is an antibody which binds to hG-CSFR expressed on the surface of a cell at an affinity of at least about 3 nM. In one example, the protein is an antibody which binds to hG-CSFR expressed on the surface of a cell at an affinity of at least about 2 nM. In one example, the protein is an antibody which binds to hG-CSFR expressed on the surface of a cell at an affinity of at least about 1 nM.

In one example, the protein is an antibody which inhibits G-CSF-induced proliferation of a BaF3 cell expressing hG-CSFR with an IC50 of at least about 5 nM. In one example, the protein is an antibody which inhibits G-CSF-induced proliferation of a BaF3 cell expressing hG-CSFR with an IC50 of at least about 4 nM. In one example, the protein is an antibody which inhibits G-CSF-induced proliferation of a BaF3 cell expressing hG-CSFR with an IC50 of at least about 3 nM. In one example, the protein is an antibody which inhibits G-CSF-induced proliferation of a BaF3 cell expressing hG-CSFR with an IC50 of at least about 2 nM. In one example, the protein is an antibody which inhibits G-CSF-induced proliferation of a BaF3 cell expressing hG-CSFR with an IC50 of at least about 1 nM. In one example, the protein is an antibody which inhibits G-CSF-induced proliferation of a BaF3 cell expressing hG-CSFR with an IC50 of at least about 0.5 nM.

In one example, the protein is chimeric, de-immunized, humanized, human or primatized. In one example, the protein or antibody is human.

In one example, the protein comprises an antibody variable region that competitively inhibits the binding of antibody C1.2G comprising a heavy chain variable region ($V_H$) comprising a sequence set forth in SEQ ID NO: 4 and a light chain variable region ($V_L$) comprising a sequence set forth in SEQ ID NO: 5 to G-CSFR.

In one example, the protein binds to an epitope comprising residues within one or two or three or four regions selected from 111-115, 170-176, 218-234 and/or 286-300 of SEQ ID NO: 1.

In one example, the protein is an antibody comprising a heavy chain variable region (VH) comprising an amino acid sequence set forth in SEQ ID NO: 4 and a light chain variable region (VL) comprising an amino acid sequence set forth in SEQ ID NO: 5.

In one example, the protein is an antibody comprising a VH comprising an amino acid sequence set forth in SEQ ID NO: 2 and a VL comprising an amino acid sequence set forth in SEQ ID NO: 3.

In one example, the protein is an antibody comprising a VH comprising three CDRs of a VH comprising an amino acid sequence set forth in SEQ ID NO: 4 and a VL comprising three CDRs of a VL comprising an amino acid sequence set forth in SEQ ID NO: 5.

In one example, the protein is an antibody comprising a VH comprising three CDRs of a VH comprising an amino acid sequence set forth in SEQ ID NO: 2 and a VL comprising three CDRs of a VL comprising an amino acid sequence set forth in SEQ ID NO: 3.

In one example, the protein is an antibody comprising:
  (i) a heavy chain comprising an amino acid sequence set forth in SEQ ID NO: 14 or 18 and a light chain comprising an amino acid sequence set forth in SEQ ID NO: 15; or
  (ii) one heavy chain comprising an amino acid sequence set forth in SEQ ID NO: 14 and one heavy chain comprising an amino acid sequence set forth in SEQ ID NO: 18 and two light chains comprising an amino acid sequence set forth in SEQ ID NO: 15.

KEY TO SEQUENCE LISTING

SEQ ID NO: 1—amino acids 25-335 of *Homo sapiens* G-CSFR (hG-CSFR) with a C-terminal polyhistidine tag
SEQ ID NO: 2—$V_H$ of C1.2
SEQ ID NO: 3—$V_L$ of C1.2
SEQ ID NO: 4—$V_H$ of C1.2G
SEQ ID NO: 5—$V_L$ of C1.2G
SEQ ID NO: 6—HCDR1 of C1.2
SEQ ID NO: 7—HCDR2 of C1.2
SEQ ID NO: 8—HCDR3 of C1.2
SEQ ID NO: 9—LCDR1 of C1.2
SEQ ID NO: 10—LCDR2 of C1.2
SEQ ID NO: 11—LCDR3 of C1.2
SEQ ID NO: 12—consensus sequence of HCDR3 of C1.2
SEQ ID NO: 13—consensus sequence of LCDR3 of C1.2
SEQ ID NO: 14—Heavy chain of C1.2G with stabilized IgG4 constant region SEQ ID NO: 15—Light chain of C1.2G with kappa constant region SEQ ID NO: 16—sequence of exemplary h-G-CSFR SEQ ID NO: 17—polypeptide comprising Ig and CRH domains of *Macaca fascicularis* G-CSFR (cynoG-CSFR) with a C-terminal polyhistidine tag SEQ ID NO: 18—Heavy chain of C1.2G with stabilized IgG4 constant region and lacking C-terminal lysine.

DETAILED DESCRIPTION

General

Figure 1:
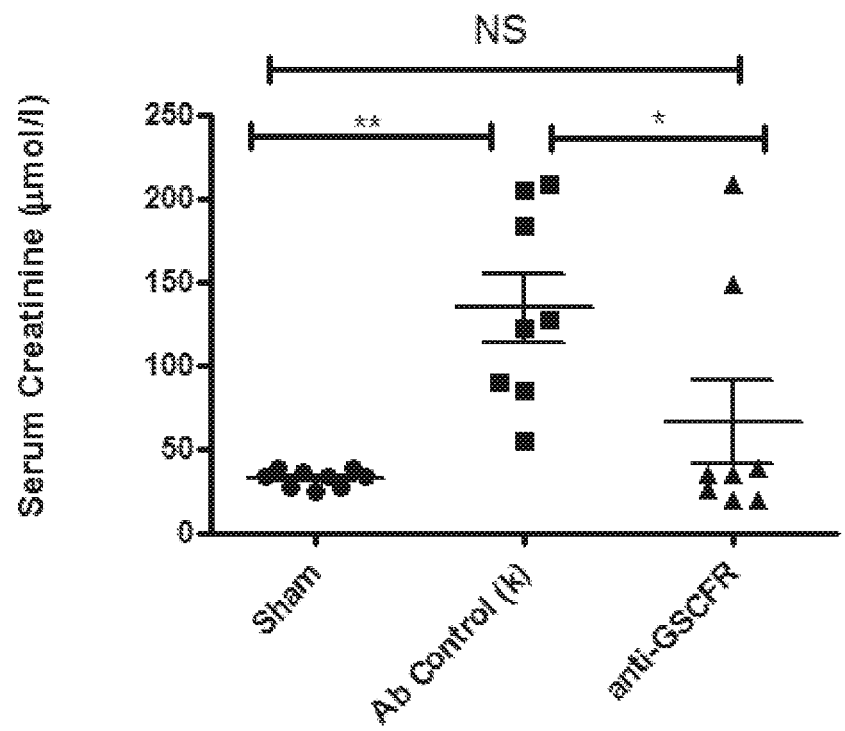
FIG. 1 is a graphical representation of serum creatinine concentrations 24 hours post reperfusion in the renal warm ischemia-reperfusion injury model. Treatment of mice with 100 μg of the anti-G-CSFR antibody VR81 significantly reduced serum creatinine concentrations compared to treatment of mice with 100 μg of an isotype control antibody. One-Way ANOVA (with Bonferroni correction), *$p<0.05$, ***$p<0.005$ ($n=8$ mice per group). The results are representative of two independent experiments—see also FIG. 7.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

A "compound", as contemplated by the present disclosure, can take any of a variety of forms including natural compounds, chemical small molecule compounds or biological compounds or macromolecules. Exemplary compounds include an antibody or an antigen binding fragment of an antibody, a nucleic acid, a polypeptide, a peptide, and a small molecule.

Reference herein to "granulocyte colony-stimulating factor" (G-CSF) includes native forms of G-CSF, mutant forms thereof, e.g., filgrastim and pegylated forms of G-CSF or filgrastim. This term also encompasses mutant forms of G-CSF retaining activity to bind to G-CSFR (e.g., human G-CSFR) and induce signaling.

G-CSF is a major regulator of granulocyte production. G-CSF is produced by bone marrow stromal cells, endothelial cells, macrophages, and fibroblasts, and production is induced by inflammatory stimuli. G-CSF acts through the G-CSF receptor (G-CSFR), which is expressed on early myeloid progenitors, mature neutrophils, monocytes/macrophages, T and B lymphocytes and endothelial cells.

For the purposes of nomenclature only and not limitation, an exemplary sequence of a human G-CSFR is set out in NCBI Reference Sequence: NP_000751.1 (and set out in SEQ ID NO: 16). The sequence of G-CSFR from other species can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human G-CSFR may be abbreviated to hG-CSFR and reference to cynomolgus monkey G-CSFR may be abbreviated to cynoG-CSFR. Reference to soluble G-CSFR refers to polypeptides comprising the ligand binding region of G-CSFR. The Ig and CRH domains of the G-CSFR are involved in ligand binding and receptor dimerization (Layton et al., *J. Biol Chem.*, 272: 29735-29741, 1997 and Fukunaga et al, *EMBO J.* 10: 2855-2865, 1991). Soluble forms of G-CSFR comprising these portions of the receptor have been used in various studies of the receptor and mutation of the free cysteines at positions 78, 163, and 228 of the receptor assists in expression and isolation of the soluble receptor polypeptide (Mine et al., *Biochem.*, 43: 2458-2464 2004) without affecting ligand binding.

As used herein, the term "ischemia-reperfusion injury" refers to tissue or organ damage caused when blood supply returns to the tissue or organ after a period of ischemia or lack of oxygen (anoxia or hypoxia). The absence of oxygen and nutrients from blood during the ischemic period creates a condition in which the restoration of circulation results in inflammation and oxidative damage through the induction of oxidative stress rather than restoration of normal function. Ischemia-reperfusion injury (IRI) is also known as "reperfusion injury", "reperfusion insult", and "reoxygenation injury". As used herein, "ischemia-reperfusion injury" includes both warm ischemia-reperfusion injury and cold ischemia-reperfusion injury.

As used herein, the term "ischemia" (also known as "ischaemia") refers to a restriction in blood supply to tissues, causing a shortage of oxygen and glucose needed for cellular metabolism, as well as causing a buildup and reduced removal of metabolic waste.

The term "reperfusion", as used herein, relates to the restoration of blood flow or oxygen to the tissue.

As used herein, the term "condition" refers to a disruption of or interference with normal function, and is not to be limited to any specific condition, and will include diseases or disorders.

As used herein, the terms "preventing", "prevent" or "prevention" include administering a compound of the disclosure to thereby stop or hinder, at least partially, the development of at least one symptom of a condition. This term also encompasses treatment of a subject in remission to prevent or hinder relapse.

As used herein, the terms "treating", "treat" or "treatment" include administering a compound described herein to thereby reduce or eliminate at least one symptom of a specified disease or condition.

As used herein, the term "neutropenia" is used to refer to an absolute neutrophil count (ANC) below the lower limit of normal range, for example an ANC of less than 2000 cells/μL blood, or less than 1500 cells/μL blood, or less than 1000 cells/μL blood, for example less than 500 cells/μL blood (see Sibille et al. 2010 Br J Clin Pharmacol 70(5): 736-748). In some examples, the compound that inhibits G-CSF signaling is administered in an amount that does not cause severe neutropenia. As used herein, the term "severe neutropenia" is used to refer to an absolute neutrophil count (ANC) of less than 1000 cells/μL blood.

As used herein, the term "subject" shall be taken to mean any animal including humans, for example a mammal. Exemplary subjects include but are not limited to humans and non-human primates. For example, the subject is a human.

It will be apparent to the skilled person from the foregoing paragraph that a donor (e.g., an organ donor) or a recipient (e.g., an organ recipient) includes mammals, for example humans.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

As used herein, the term "antigen binding site" shall be taken to mean a structure formed by a protein that is capable of binding or specifically binding to an antigen. The antigen binding site need not be a series of contiguous amino acids, or even amino acids in a single polypeptide chain. For example, in a Fv produced from two different polypeptide chains the antigen binding site is made up of a series of amino acids of a $V_L$ and a $V_H$ that interact with the antigen and that are generally, however not always in the one or more of the CDRs in each variable region. In some examples, an antigen binding site is a $V_H$ or a $V_L$ or a Fv.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are necessary for antigen binding. Each variable region typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309: 657-670, 2001. For example, according to the numbering system of Kabat, $V_H$ framework regions (FRs) and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including those discussed above. In one example, reference herein to a CDR (or a FR) is in respect of those regions according to the Kabat numbering system.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a compound or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a compound of the disclosure reacts or associates more frequently, more rapidly, with greater duration and/or with greater affinity with a particular antigen or cell expressing same than it does with alternative antigens or cells. For example, a compound binds to G-CSFR (e.g., hG-CSFR) with materially greater affinity (e.g., 20 fold or 40 fold or 60 fold or 80 fold to 100 fold or 150 fold or 200 fold) than it does to other cytokine receptor or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

A protein or antibody may be considered to "preferentially bind" to a polypeptide if it binds that polypeptide with a dissociation constant ($K_D$) that is less than the protein's or antibody's $K_D$ for another polypeptide. In one example, a protein or antibody is considered to preferentially bind to a polypeptide if it binds the polypeptide with an affinity (i.e., $K_D$) that is at least about 20 fold or 40 fold or 60 fold or 80 fold or 100 fold or 120 fold or 140 fold or 160 fold more than the protein's or antibody's $K_D$ for another polypeptide.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "$IC_{50}$ of at least about" will be understood to mean that the $IC_{50}$ is equal to the recited value or greater (i.e., the value recited as the $IC_{50}$ is lower), i.e., an $IC_{50}$ of 2 nM is greater than an $IC_{50}$ of 3 nM. Stated another way, this term could be "an $IC_{50}$ of X or less", wherein X is a value recited herein.

As used herein, the term "epitope" (syn. "antigenic determinant") shall be understood to mean a region of hG-CSFR to which a protein comprising an antigen binding site of an antibody binds. This term is not necessarily limited to the specific residues or structure to which the protein makes contact. For example, this term includes the region spanning amino acids contacted by the protein and/or 5-10 or 2-5 or 1-3 amino acids outside of this region. In some examples, the epitope comprises a series of discontinuous amino acids that are positioned close to one another when hG-CSFR is folded, i.e., a "conformational epitope". For example, a conformational epitope comprises amino acids in one or more or two or more or all of the regions corresponding to 111-115, 170-176, 218-234 and/or 286-300 of SEQ ID NO: 1. The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that a protein of the disclosure (or an antigen binding site thereof) reduces or prevents binding of a recited antibody or protein to G-CSFR, e.g., to hG-CSFR. This may be due to the protein (or antigen binding site) and antibody binding to the same or an overlapping epitope. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to G-CSFR either in the presence or absence of the protein. If less antibody binds in the presence of the protein than in the absence of the protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a protein (or antigen binding site thereof) that binds to one epitope to competitively inhibit the binding of a protein (or antigen binding site) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a compound is capable of blocking, reducing or preventing G-CSF-mediated signaling in a cell through the G-CSFR. Methods for determining neutralization are known in the art and/or described herein.

Preventing or Treating Ischemia-Reperfusion Injury

The present disclosure provides, for example, a method for preventing or treating ischemia-reperfusion injury in a subject comprising administering a compound that inhibits granulocyte colony stimulating factor G-CSF signaling. For example, the compound binds to G-CSF or G-CSFR.

An ischemia-reperfusion injury can be caused by a natural event (e.g., restoration of blood flow following a myocardial infarction or stroke), a trauma, a tumor, or by one or more surgical procedures or other therapeutic interventions that restore blood flow or oxygen to a tissue or organ that has been subjected to a diminished supply of blood or oxygen.

In one example, the ischemia-reperfusion injury is caused by a surgical procedure. Such surgical procedures include, for example, coronary artery bypass, graft surgery, coronary angioplasty, organ transplant surgery and the like (e.g., cardiopulmonary bypass surgery).

In some examples, the ischemia and/or reperfusion injury is due to or associated with organ transplantation, cold organ storage, brain death, atherosclerosis, thrombosis, thromboembolism, lipid-embolism, trauma, bleeding, a stent, surgery, angioplasty, bypass surgery, total ischemia, myocardial infarction, stroke, peripheral vascular disease, surgery, sepsis, or combinations thereof.

In some examples, the ischemia-reperfusion injury is due to or associated with organ transplantation. In some examples, the organ is a solid organ. In some examples, the organ transplantation is a kidney transplantation. In some examples, the organ transplantation is a liver transplantation. In some examples, the organ transplantation is a heart transplantation. In some examples, the organ transplantation is a pancreas transplantation. In one example, the organ transplantation is a lung transplantation. In one example, the organ transplantation is a stomach transplantation. In one example, the organ transplantation is a intestine transplantation. In one example, the organ transplantation is a testis transplantation.

In one example, the ischemia-reperfusion injury is due to or associated with a tissue transplantation. In one example, the tissue transplantation is a blood vessel transplantation. In one example, the tissue transplantation is a skin transplantation, for example vascularized skin. In one example, the tissue transplantation is a pancreatic islet transplantation.

Effects of ischemia-reperfusion injury include organ dysfunction, infarct, inflammation, oxidative damage, mitochondrial membrane potential damage, apoptosis, reperfusion-related arrhythmia, cardiac stunning, cardiac lipotoxicity, ischemia-derived scar formation, and combinations thereof. For ischemia-reperfusion injury due to or associated with kidney transplantation, effects also include acute kidney injury and delayed graft function (DGF).

In some examples, the method of the present disclosure prevents or reduces the likelihood of acute kidney injury following transplantation. For example, the method of the present disclosure prevents or reduces the risk of one or more of the following:
  an increase in plasma creatinine levels of at least ≥0.3 mg per dL (26.52 µmol per L) or ≥1.5-to twofold from baseline;
  less than about 0.5 mL of urine per kg per hour for at least six hours; and/or
  required renal replacement treatment.

In some examples, the method of the present disclosure prevents or reduces the likelihood of delayed graft function following transplantation, e.g., kidney transplantation. As the skilled person will be aware, delayed graft function is associated with poor long term graft outcomes, chronic graft rejection and/or organ survival. For example, the method of the present disclosure prevents or reduces the risk of one or more of the following:

The need for one or more hemodialysis treatments within about 7 days of transplantation before the onset of graft function;

Creatinine reduction ratio between Day 0 and Day 7 of less than 70 percent.

In some examples, the method of the present disclosure prevents or reduces the likelihood of one or more of the following:

Primary graft non-function: a condition in which the kidney never functions adequately after transplantation, and the patient continues to need dialysis despite a transplant; and/or Slow graft function: defined as serum creatinine greater than 3 milligrams (mg) per deciliter and no need for dialysis at Day 5 post-transplantation.

In some examples, the compound that inhibits G-CSF signaling is administered in an amount sufficient to reduce or prevent inflammation, e.g., in a transplanted organ. As used herein, the term "inflammation", or "inflammatory response", relates to a set of changes occurring in a tissue that undergoes inflammation. In particular, inflammation relates to the biological response to harmful stimuli, including pathogens, damaged cells or irritants. Methods to determine inflammation are known in the art and include, without limitation, measure of erythrocyte sedimentation rate (ESR), wherein a higher ESR is indicative of inflammation, measure of C-reactive protein (CRP), wherein a higher level of CRP is indicative of inflammation, and leukocyte count (increased in inflammation).

In some examples, the compound that inhibits G-CSF signaling is administered in an amount sufficient to reduce or prevent oxidative damage, e.g., in a transplanted organ. As used herein, the term "oxidative damage" relates to the biomolecular damage that can be caused by reactive species during oxygen restoration. Oxidative damage may involve lipid peroxidation, oxidative DNA damage and oxidative damage to proteins. Methods to determine lipid peroxidation include, without limitation, MDA (malondialdehyde)-TBA (thiobarbituric acid) determination by HPLC, and quantification of isoprostanes (which are specific end products of the peroxidation of polyunsaturated fatty acids) by mass spectrometry. Methods to determine DNA oxidative damage include, without limitation, measure of 8-hydroxy-2'-deoxyguanosine (8OHdG). Methods to determine oxidative damage to proteins include, without limitation, quantification of individual aminoacid oxidation products including kynurenines (from tryptophan), bityrosine (which appears to be metabolically stable and can be detected in urine), valine and leucine hydroxides, L-dihydroxyphenylalanine (L-DOPA), ortho-tyrosine, 2-oxo-histidine, glutamate semialdehyde and adipic semialdehyde, as well as the carbonyl assay (involving measurement of protein carbonyl groups). The mitochondrial membrane potential ($\Delta\psi$tal) relates to the membrane potential in the form of proton gradient across the mitochondrial inner membrane. Methods for evaluation of mitochondrial membrane potential damage are known by the skilled person and include the use of fluorescent probes for monitoring membrane potential including the JC1 dye (Cell Technology) and the measure of overall fluorescence at excitation and emission wavelengths allowing the quantification of green (485 nm and 535 nm) and red fluorescence (550 nm and 600 nm). Prolonged ischemia of any tissue or organ is known to induce mitochondrial membrane potential damage.

In some examples, the compound that inhibits G-CSF signaling is administered in an amount sufficient to reduce or prevent neutrophil and/or macrophage infiltration. As used herein, the terms "neutrophil infiltration" and "macrophage infiltration" refer to the recruitment or accumulation of neutrophils and macrophages in tissues or cells in response to a variety of substances being released at the sites of inflammatory reactions due to ischemia-reperfusion injury. For example, infiltration of neutrophils and/or macrophages can occur in donor organ tissue following organ transplantation. Methods of measuring neutrophil and/or macrophage infiltration will be known to those skilled in the art. For example, the neutrophils or macrophages can be measured directly, such as by visualisation by fluorescence microscopy, or indirectly by measuring the abundance or activity of neutrophil/macrophage specific proteins or enzymes in an affected tissue. Suitable methods for measuring neutrophil and/or macrophage infiltration are described in Soo-Jeong Yu et al Korean J Intern Med (2008) and Pulli et al PloS One (2013).

In some examples, the compound that inhibits G-CSF signaling is administered in an amount sufficient to reduce or prevent complement C5 activation. Methods for measuring complement C5a activation include, but are not limited to assessment of plasma C5a levels by enzyme-linked immunosorbent assay (ELISA).

In some examples, the compound that inhibits G-CSF signaling is administered in an amount sufficient to reduce or prevent C5b-9 deposition. Methods for measuring C5b-9 deposition include, but are not limited to analysis by immunofluorescence staining of kidney sections.

In some examples, the compound that inhibits G-CSF signaling is administered in an amount sufficient to reduce expression of one or more of the following:
interleukin 8 receptor beta (IL-8R$\beta$);
monocyte chemoattractant protein 1 (MCP-1);
kidney injury molecule 1 (KIM-1);
neutrophil gelatinase-associated lipocalin (NGAL);
interleukin 1 beta (IL-1$\beta$);
interleukin 6 (IL-6);
tumor necrosis factor alpha (TNF$\alpha$);
complement component 5a receptor 1 (C5AR1);
macrophage inflammatory protein 2-alpha (MIP2-alpha);
intercellular Adhesion Molecule 1 (ICAM-1);
E-selectin; and
C-X-C motif chemokine ligand 1 (CXCL1).

Methods for measuring the expression level of a gene will be known in the art. For example, expression level of a gene can be measured by quantifying the amount of mRNA, e.g., by northern blot or by quantitative reverse transcription PCR (qRT-PCR) as described in Riedy et al Biotechniques (1995). Alternatively, or in addition, expression level of a gene can be measured by quantifying the level of protein encoded by the gene, e.g., by enzyme-linked immunosorbent assay (ELISA), fluorescence linked immunosorbent assay (FLISA), immunofluorescence or immunoblotting (see Sambrook et al., Molecular Cloning: A Laboratory Manual, Cold Spring Harbor Laboratory Press (1989)).

In some examples, the compound that inhibits G-CSF signaling is administered in an amount sufficient to reduce or prevent delayed graft function, for example, associated with kidney transplantation. Delayed graft function is a manifestation of acute kidney injury resulting in post-transplantation oliguria, increased allograft immunogenicity and risk of acute rejection episodes, and decreased long-term survival. Suitable biomarkers for detecting delayed graft function include NGAL, KIM-1, liver-type fatty acid binding protein (L-FABP), interleukin 18 (IL-18), YKL-40 (a 40 kDa heparin- and chitin-binding glycoprotein, see eg. Hakala et al., *J Biol Chem* 1993), clusterin, and cystatin C. Such biomarkers for detecting delayed graft function are described in Malyszko et al., *Sci Rep* (2015), which is incorporated herein by reference.

In some examples, the compound that inhibits G-CSF signaling is administered in an amount sufficient to reduce or prevent an increase in serum or plasma creatinine levels. A person skilled in the art would appreciate that increased serum (or plasma) creatinine levels are an indicator of impaired kidney function. As a kidney becomes impaired for any reason, for example due to ischemia-reperfusion injury, the creatinine level in the blood will rise due to poor clearance of creatinine by the kidneys. Abnormally high levels of creatinine thus warn of possible malfunction or failure of the kidneys. Suitable methods for measuring serum (or plasma) creatinine levels will be known in the art, for example the Jaffe reaction using alkaline picrate, and are described in Peake and Whiting, Clin Biochem Rev (2006).

In some examples, the compound that inhibits G-CSF signaling is administered in an amount sufficient to reduce or prevent an increase in serum or plasma urea levels. Increased serum or plasma urea levels are an indicator of impaired kidney function, and can result from ischemia-reperfusion injury. Serum or plasma urea can be measured by any suitable method known in the art. For example, serum or plasma urea can be measured by chemical methods such as the reaction of diacetyl (generated from diacetyl monoxime and acid) with urea to form diazine, or by enzymatic methods using e.g., urease to generate and measure ammonia or glutamate dehydrogenase, in which the consumption of NADH is measured. For example, the Cell Biolabs' Urea Assay Kit is based on the Berthelot reaction in which Urea is first degraded into ammonia and carbon dioxide, which further reacts with an alkaline developer to produce a blue-green coloured product that can be measured with a standard spectrophotometric plate reader at an optical density between 580-630 nm. Suitable methods for measuring serum or plasma urea levels include those that are described in Lamb E et al., Kidney Function Tests (Chapter 25): Tietz Textbook of Clinical Chemistry and Molecular Diagnostics (2012).

In some examples, the compound that inhibits G-CSF signaling is administered in an amount sufficient to reduce or prevent an increase in urine albumin levels. Increased urine albumin levels are an indicator of impaired kidney function, and can result from ischemia-reperfusion injury. Urine albumin levels can be measured by any suitable method known in the art. For example, urine albumin levels can be measured using a microalbuminuria test.

In one example, the compound that inhibits G-CSF signaling is administered in an amount sufficient to reduce or prevent an increase in levels of blood in the subject's urine. The presence of blood in urine (also known as "haematuria") is an indicator of impaired kidney function, and can result from ischemia-reperfusion injury. Levels of blood in the subject's urine can be measured by any suitable method known in the art. For example levels of blood in the subject's urine can be measured using a urine dipstick, or by detecting the presence of red blood cells by microscopic examination of a urine sample.

Antibodies

In one example, a compound as described herein according to any example is a protein comprising an antigen binding site of an antibody. In some examples, the compound that inhibits G-CSF signaling is an antibody. In some examples, the antibody binds to G-CSFR. In some examples, the antibody binds to G-CSF.

Methods for generating antibodies are known in the art and/or described in Harlow and Lane (editors) Antibodies: A Laboratory Manual, Cold Spring Harbor Laboratory, (1988). Generally, in such methods G-CSFR or G-CSF (e.g., hG-CSFR or hG-CSF) or a region thereof (e.g., an extracellular domain) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

Monoclonal antibodies are one exemplary form of an antibody contemplated by the present disclosure. The term "monoclonal antibody" or "mAb" refers to a homogeneous antibody population capable of binding to the same antigen(s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

Alternatively, ABL-MYC technology (NeoClone, Madison WI 53713, USA) is used to produce cell lines secreting MAbs (e.g., as described in Largaespada et al, *J. Immunol. Methods*. 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

The antibody of the present disclosure may be a synthetic antibody. For example, the antibody is a chimeric antibody, a humanized antibody, a human antibody or a de-immunized antibody.

In one example, an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Methods for producing chimeric antibodies are described in, e.g., U.S. Pat. Nos. 4,816,567; and 5,807,715.

The antibodies of the present disclosure may be humanized or human.

The term "humanized antibody" shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from the non-human antibody grafted onto appropriate FRs in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues.

Methods for humanizing non-human antibodies or parts thereof (e.g., variable regions) are known in the art. Humanization can be performed following the method of U.S. Pat. No. 5,225,539, or U.S. Pat. No. 5,585,089. Other methods for humanizing an antibody are not excluded.

The term "human antibody" as used herein refers to antibodies having variable regions (e.g. $V_H$, $V_L$) and, optionally constant regions derived from or corresponding to sequences found in humans, e.g. in the human germline or somatic cells.

Exemplary human antibodies are described herein and include C1.2 and C1.2G and/or variable regions thereof. These human antibodies provide an advantage of reduced immunogenicity in a human compared to non-human antibodies. Exemplary antibodies are described in WO2012171057, which is incorporated herein by reference.

Antibody Binding Domain Containing Proteins

Single-Domain Antibodies

In some examples, a compound of the disclosure is a protein that is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e.g., U.S. Pat. No. 6,248,516).

Diabodies, Triabodies, Tetrabodies

In some examples, a protein of the disclosure is or comprises a diabody, triabody, tetrabody or higher order protein complex such as those described in WO98/044001 and/or WO94/007921.

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Antibody Fragments

The present disclosure also contemplates other antibodies and antibody fragments, such as:
 (i) "key and hole" bispecific proteins as described in U.S. Pat. No. 5,731,168;
 (ii) heteroconjugate proteins, e.g., as described in U.S. Pat. No. 4,676,980;
 (iii) heteroconjugate proteins produced using a chemical cross-linker, e.g., as described in U.S. Pat. No. 4,676,980; and
 (iv) $Fab_3$ (e.g., as described in EP19930302894).

V-Like Proteins

An example of a compound of the disclosure is a T-cell receptor. T cell receptors have two V-domains that combine into a structure similar to the Fv module of an antibody. Novotny et al., Proc Natl Acad Sci USA 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}Fn3$) domain of human fibronectin in which the loop regions are altered to confer antigen binding. For example, three loops at one end of the β-sandwich of the $^{10}Fn3$ domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid-sheet secondary structure with a plurality of loops at the open end of the conical structure which can be engineered to bind to an antigen. Such engineered lipocalins are known as anticalins. For further description of anticalins see U.S. Pat. No. 7,250,297B1 or US20070224633.

Affibodies

In a further example, a compound of the disclosure is an affibody. An affibody is a scaffold derived from the Z domain (antigen binding domain) of Protein A of Staphylococcus aureus which can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a 1-turn. They can be engineered to bind different target antigens by randomizing residues in the first α-helix and a β-turn of each repeat. Their binding interface can be increased by increasing the number of modules (a method of affinity maturation). For further details see US20040132028.

Soluble G-CSFR

The present disclosure also contemplates a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al, Acta Crystallograph Sect F *Struct Biol Cryst Commun.* 61(Pt 8):788-790, 2005.

De-Immunized Antibodies and Proteins

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO2000/34317, WO2004/108158 and WO2004/064724.

Methods for introducing suitable mutations and expressing and assaying the resulting protein will be apparent to the skilled artisan based on the description herein.

Mutations to Proteins

The present disclosure also contemplates mutant forms of a protein of the disclosure. In this regard, data presented herein indicate sites within a CDR of a protein of the disclosure that can be changed in addition to exemplary changes that can be made. The skilled person will understand that changes can additionally or alternatively be made within a framework region of a variable region containing protein without inhibiting or significantly reducing its function in the context of the present disclosure.

For example, such a mutant protein comprises one or more conservative amino acid substitutions compared to a sequence set forth herein. In some examples, the protein comprises 30 or fewer or 20 or fewer or 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In one example, a mutant protein has only, or not more than, one or two or three or four or five or six conservative amino acid changes when compared to a naturally occurring protein. Details of conservative amino acid changes are provided below. As the skilled person would be aware, e.g., from the disclosure herein, such minor changes can reasonably be predicted not to alter the activity of the protein.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

The present disclosure also contemplates non-conservative amino acid changes (e.g., substitutions) in a protein of the present disclosure, e.g., in a CDR, such as CDR3. For example, the present inventors have identified several non-conservative amino acid substitutions that can be made while retaining an activity of a protein of the disclosure. In one example, the protein comprises fewer than 6 or 5 or 4 or 3 or 2 or 1 non-conservative amino acid substitutions, e.g., in a CDR3, such as in a CDR3.

The present disclosure also contemplates one or more insertions or deletions compared to a sequence set forth herein. In some examples, the protein comprises 10 or fewer, e.g., 9 or 8 or 7 or 6 or 5 or 4 or 3 or 2 insertions and/or deletions.

Constant Regions

The present disclosure encompasses proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA,* 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present disclosure also contemplates additional modifications to an antibody or protein of the disclosure.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

In one example, the protein of the disclosure additionally comprises albumin, a functional fragment or variant thereof. In one example, the albumin, functional fragment or variant thereof is serum albumin, such as human serum albumin. In one example, the albumin, functional fragment or variant thereof, comprises one or more amino acid substitutions, deletions or insertions, e.g., no more than 5 or 4 or 3 or 2 or 1 substitutions. Amino acid substitutions suitable for use in the present disclosure will be apparent to the skilled person and include naturally-occurring substitutions and engineered substitutions such as those described, for example, in WO2011051489, WO2014072481, WO2011103076, WO2012112188, WO2013075066, WO2015063611 and WO2014179657.

Protein Production

In one example, a protein described herein according to any example is produced by culturing a hybridoma under conditions sufficient to produce the protein, e.g., as described herein and/or as is known in the art.

Recombinant Expression

In another example, a protein described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/0-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris*, *Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMl-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Nucleic Acid-Based G-CSF Signaling Inhibitors

In one example of the disclosure, therapeutic and/or prophylactic methods as described herein according to any example of the disclosure involve reducing expression of G-CSF and/or G-CSFR. For example, such a method involves administering a compound that reduces transcription and/or translation of a nucleic acid encoding G-CSF or G-CSFR. In one example, the compound that inhibits G-CSF signaling is a nucleic acid, e.g., an antisense polynucleotide, a ribozyme, a PNA, an interfering RNA, a siRNA, a microRNA.

In another example, the compound that inhibits G-CSF signaling is a nucleic acid encoding a protein compound that inhibits G-CSF signaling (e.g., an antibody or antigen binding fragment thereof).

Antisense Nucleic Acids

The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding G-CSF or G-CSFR, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding G-CSF or G-CSFR. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against G-CSF or G-CSFR are described, for example, in WO2011032204.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding G-CSF or G-CSFR. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815. Such dsRNA molecules for RNAi include, but are not limited to short hairpin RNA (shRNA) and bi-functional shRNA.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search.

Aptamers

In another example, a compound is a nucleic acid aptamer (adaptable oligomer). Aptamers are single stranded oligonucleotides or oligonucleotide analogs that are capable of forming a secondary and/or tertiary structure that provides the ability to bind to a particular target molecule, such as a protein or a small molecule, e.g., G-CSF or G-CSFR. Thus, aptamers are the oligonucleotide analogy to antibodies. In general, aptamers comprise about 15 to about 100 nucleotides, such as about 15 to about 40 nucleotides, for example about 20 to about 40 nucleotides, since oligonucleotides of a length that falls within these ranges can be prepared by conventional techniques.

An aptamer can be isolated from or identified from a library of aptamers. An aptamer library is produced, for example, by cloning random oligonucleotides into a vector (or an expression vector in the case of an RNA aptamer), wherein the random sequence is flanked by known sequences that provide the site of binding for PCR primers. An aptamer that provides the desired biological activity (e.g., binds specifically to G-CSF or G-CSFR) is selected. An aptamer with increased activity is selected, for example, using SELEX (Sytematic Evolution of Ligands by EXponential enrichment). Suitable methods for producing and/or screening an aptamer library are described, for example, in Elloington and Szostak, *Nature* 346:818-22, 1990; U.S. Pat. No. 5,270,163; and/or U.S. Pat. No. 5,475,096.

Assaying Activity of a Compound

Binding to G-CSFR and Mutants Thereof

It will be apparent to the skilled artisan from the disclosure herein that some compounds of the present disclosure bind to the ligand binding domain of hG-CSFR and to specific mutant forms of the ligand binding domain of hG-CSFR (e.g., SEQ ID NO: 1 without or with certain point mutations) and/or bind to both human and cynomolgus monkey G-CSFR. Methods for assessing binding to a protein are known in the art, e.g., as described in Scopes (In: Protein purification: principles and practice, Third Edition, Springer Verlag, 1994). Such a method generally involves labeling the protein and contacting it with immobilized compound. Following washing to remove non-specific bound protein, the amount of label and, as a consequence, bound protein is detected. Of course, the protein can be immobilized and the compound that inhibits G-CSF signaling labeled. Panning-type assays can also be used. Alternatively, or additionally, surface plasmon resonance assays can be used.

The assays described above can also be used to detect the level of binding of a compound to hG-CSFR or a ligand binding domain thereof (e.g., SEQ ID NO: 1) or mutant form thereof.

In one example, a protein of the present disclosure binds to a polypeptide of SEQ ID NO: 1 in which an alanine is substituted for the lysine at position 167 of SEQ ID NO: 1 and/or in which an alanine is substituted for the histidine at position 168 of SEQ ID NO: 1 at substantially the same level (e.g., within 10% or 5% or 1%) as it binds to SEQ ID NO: 1.

In one example, a protein of the present disclosure binds to a polypeptide of SEQ ID NO: 1 in which an alanine is substituted for the arginine at position 287 of SEQ ID NO: 1 at a level at least about 100 fold or 150 fold or 160 fold or 200 fold lower than it binds to a polypeptide of SEQ ID NO: 1. In one example, a protein of the present disclosure binds to a polypeptide of SEQ ID NO: 1 in which an alanine is substituted for the arginine at position 287 of SEQ ID NO: 1 at a level at least about 160 fold lower than it binds to a polypeptide of SEQ ID NO: 1.

In one example, a protein of the present disclosure binds to a polypeptide of SEQ ID NO: 1 in which an alanine is substituted for the histidine at position 237 of SEQ ID NO: 1 at a level at least about 20 fold or 40 fold or 50 fold or 60 fold lower than it binds to a polypeptide of SEQ ID NO: 1. In one example, a protein of the present disclosure binds to a polypeptide of SEQ ID NO: 1 in which an alanine is substituted for the histidine at position 237 of SEQ ID NO: 1 at a level at least about 50 fold lower than it binds to a polypeptide of SEQ ID NO: 1.

In one example, a protein of the present disclosure binds to a polypeptide of SEQ ID NO: 1 in which an alanine is substituted for the methionine at position 198 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the methionine at position 198 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the tyrosine at position 172 of SEQ ID NO: 1 at a level at least about 20 fold or 30 fold or 40 fold lower than it binds to a polypeptide of SEQ ID NO: 1. In one example, a protein of the present disclosure binds to a polypeptide of SEQ ID NO: 1 in which an alanine is substituted for the tyrosine at position 172 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the leucine at position 171 of SEQ ID NO: 1 at a level at least about 100 fold or 120 fold or 130 fold or 140 fold lower than it binds to a polypeptide of SEQ ID NO: 1. In one example, a protein of the present disclosure binds to a polypeptide of SEQ ID NO: 1 in which an alanine is substituted for the leucine at position 171 of SEQ ID NO: 1 at a level at least about 140 fold lower than it binds to a polypeptide of SEQ ID NO: 1.

In one example, a protein of the present disclosure binds to a polypeptide of SEQ ID NO: 1 in which an alanine is substituted for the leucine at a position 111 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the leucine at a position 111 of SEQ ID NO: 1 at a level at least about 60 fold lower than it binds to a polypeptide of SEQ ID NO: 1.

In one example, a protein of the present disclosure binds to a polypeptide of SEQ ID NO: 1 in which an alanine is substituted for the histidine at position 168 of SEQ ID NO: 1 at a level no more than 5 fold or 4 fold or 3 fold or 2 fold or 1 fold lower than it binds to a polypeptide of SEQ ID NO: 1.

In one example, a protein of the present disclosure binds to a polypeptide of SEQ ID NO: 1 in which an alanine is substituted for the lysine at position 167 of SEQ ID NO: 1 at a level no more than 5 fold or 4 fold or 3 fold or 2 fold or 1 fold lower than it binds to a polypeptide of SEQ ID NO: 1.

The level of binding is conveniently determined using a biosensor.

The present disclosure contemplates any combination of the foregoing characteristics. In one example, a protein described herein has all of the binding characteristics set forth in the preceding seven paragraphs.

Epitope Mapping

In another example, the epitope bound by a protein described herein is mapped. Epitope mapping methods will be apparent to the skilled artisan. For example, a series of overlapping peptides spanning the hG-CSFR sequence or a region thereof comprising an epitope of interest, e.g., peptides comprising 10-15 amino acids are produced. The protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within hG-CSFR are mutated, e.g., by alanine scanning mutagenesis, and mutations that reduce or prevent protein binding are determined. Any mutation that reduces or prevents binding of the protein is likely to be within the epitope bound by the protein.

A further method is exemplified herein, and involves binding hG-CSFR or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in hG-CSFR or a region thereof to deutrons and binding the resulting protein to an immobilized protein of the present disclosure. The deutrons are then converted back to hydrogen, the hG-CSFR or region thereof isolated, digested with enzymes and analyzed, e.g., using mass spectrometry to identify those regions comprising deutrons, which would have been protected from conversion to hydrogen by the binding of a protein described herein.

Optionally, the dissociation constant (Kd) of a protein for hG-CSFR or an epitope thereof is determined. The "Kd" or "Kd value" for a hG-CSFR binding protein is in one example measured by a radiolabeled or fluorescently-labeled hG-CSFR binding assay. This assay equilibrates the protein with a minimal concentration of labeled G-CSFR in the presence of a titration series of unlabeled hG-CSFR. Following washing to remove unbound hG-CSFR, the amount of label is determined, which is indicative of the Kd of the protein.

According to another example the Kd or Kd value is measured by using surface plasmon resonance assays, e.g., using BIAcore surface plasmon resonance (BIAcore, Inc., Piscataway, NJ) with immobilized hG-CSFR or a region thereof.

In some examples, proteins having a similar Kd or a higher Kd than C1.2 or C1.2G are selected, because they are likely to compete for binding to hG-CSFR.

Determining Competitive Binding

Assays for determining a protein that competitively inhibits binding of monoclonal antibody C1.2 or C1.2G will be apparent to the skilled artisan. For example, C1.2 or C1.2G is conjugated to a detectable label, e.g., a fluorescent label or a radioactive label. The labeled antibody and the test protein are then mixed and contacted with hG-CSFR or a region thereof (e.g., a polypeptide comprising SEQ ID NO: 1) or a cell expressing same. The level of labeled C1.2 or C1.2G is then determined and compared to the level determined when the labeled antibody is contacted with the hG-CSFR, region or cells in the absence of the protein. If the level of labeled C1.2 or C1.2G is reduced in the presence of the test protein compared to the absence of the protein, the protein is considered to competitively inhibit binding of C1.2 or C1.2G to hG-CSFR.

Optionally, the test protein is conjugated to different label to C1.2 or C1.2G. This alternate labeling permits detection of the level of binding of the test protein to hG-CSFR or the region thereof or the cell.

In another example, the protein is permitted to bind to hG-CSFR or a region thereof (e.g., a polypeptide comprising SEQ ID NO: 1) or a cell expressing same prior to contacting the hG-CSFR, region or cell with C1.2 or C1.2G. A reduction in the amount of bound C1.2 or C1.2G in the presence of the protein compared to in the absence of the protein indicates that the protein competitively inhibits C1.2 or C1.2G binding to hG-CSFR. A reciprocal assay can also be performed using labeled protein and first allowing C1.2 or C1.2G to bind to G-CSFR. In this case, a reduced amount of labeled protein bound to hG-CSFR in the presence of C1.2 or C1.2G compared to in the absence of C1.2 or C1.2G indicates that the protein competitively inhibits binding of C1.2 or C1.2G to hG-CSFR.

Any of the foregoing assays can be performed with a mutant form of hG-CSFR and/or SEQ ID NO: 1 and/or a ligand binding region of hG-CSFR to which C1.2 or C1.2G binds, e.g., as described herein.

Determining Neutralization

In some examples of the present disclosure, a compound is capable of neutralizing hG-CSFR signaling.

Various assays are known in the art for assessing the ability of a compound to neutralize signaling of a ligand through a receptor.

In one example, the compound that inhibits G-CSF signaling reduces or prevents G-CSF binding to the hG-CSFR. These assays can be performed as a competitive binding assay as described herein using labeled G-CSF and/or labeled protein.

In another example, the compound that inhibits G-CSF signaling reduces formation of CFU-G when CD34$^+$ bone marrow cells are cultured in the presence of G-CSF. In such assays, CD34$^+$ bone marrow cells are cultured in a semi-solid cell culture medium in the presence of G-CSF (e.g., about 10 ng/ml cell culture medium) and, optionally stem cell factor (e.g., about 10 ng/ml cell culture medium) in the presence or absence of a test compound. After a sufficient time for granulocyte clones (CFU-G) to form, the number of clones or colonies is determined. A reduction in the number of colonies in the presence of the compound that inhibits G-CSF signaling compared to in the absence of the compound that inhibits G-CSF signaling indicates that the compound that inhibits G-CSF signaling neutralizes G-CSF signaling. By testing multiple concentrations of the compound that inhibits G-CSF signaling an $IC_{50}$ is determined, i.e., a concentration at which 50% of the maximum inhibition of CFU-G formation occurs. In one example, the $IC_{50}$ is 0.2 nM or less, such as 0.1 nM or less, for example, 0.09 nM or less, or 0.08 nM or less, or 0.07 nM or less, or 0.06 nM or less or 0.05 nM or less. In one example, the $IC_{50}$ is 0.04 nM or less. In another example, the $IC_{50}$ is 0.02 nM or less. The foregoing $IC_{50}$s relate to any CFU-G assay described herein.

In a further example, the compound that inhibits G-CSF signaling reduces proliferation of cells (e.g., BaF3 cells) expressing hG-CSFR which are cultured in the presence of G-CSF. Cells are cultured in the presence of G-CSF (e.g., 0.5 ng/ml) and the presence or absence of a test compound. Methods for assessing cell proliferation are known in the art and include, for example, MTT reduction and thymidine incorporation. A compound that reduces the level of proliferation compared to the level observed in the absence of the compound is considered to neutralize G-CSF signaling. By testing multiple concentrations of the compound an $IC_{50}$ is determined, i.e., a concentration at which 50% of the maximum inhibition of cell proliferation occurs. In one example, the $IC_{50}$ is 6 nM or less, such as 5.9 nM or less. In another example, the $IC_{50}$ is 2 nM or less or 1 nM or less or 0.7 nM or cell or 0.6 nM or less or 0.5 nM or less. The foregoing $IC_{50}$s relate to any cell proliferation assay described herein.

In a further example, the compound that inhibits G-CSF signaling reduces mobilization of hematopoietic stem cells and/or endothelial progenitor cells in vivo following G-CSF administration and/or reduces the number of neutrophils in vivo, e.g., following G-CSF administration (however this is not essential). For example, the compound that inhibits G-CSF signaling is administered, optionally before, at the time of or after administration of G-CSF or a modified form thereof (e.g., PEGylated G-CSF or filgrastim). The number of hematopoietic stem cells (e.g., expressing CD34 and/or Thy1) and/or endothelial progenitor cells (e.g., expressing CD34 and VEGFR2) and/or neutrophils (identified morphologically and/or expressing e.g., CD10, CD14, CD31 and/or CD88) is assessed. A compound that reduces the level of the cell(s) compared to the level observed in the absence of the compound is considered to neutralize G-CSF signaling. In one example, the compound that inhibits G-CSF signaling reduces the number of neutrophils without inducing neutropenia.

Other methods for assessing neutralization of G-CSF signaling are contemplated by the present disclosure.

Determining Effector Function

As discussed herein, some proteins of the present disclosure have reduced effector function. Methods for assessing ADCC activity are known in the art.

In one example, the level of ADCC activity is assessed using a $^{51}$Cr release assay, an europium release assay or a $^{35}$S release assay. In each of these assays, cells expressing G-CSFR are cultured with one or more of the recited compounds that inhibit G-CSF signaling for a time and under conditions sufficient for the compound to be taken up by the cell. In the case of a $^{35}$S release assay, cells expressing hG-CSFR can be cultured with $^{35}$S-labeled methionine and/or cysteine for a time sufficient for the labeled amino acids to be incorporated into newly synthesized proteins. Cells are then cultured in the presence or absence of the protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the protein compared to in the absence of protein (or a reduced level of the compound compared to the level observed in the presence of an anti-hG-CSFR antibody comprising a human IgG1 Fc) indicates that the protein has reduced effector function. Exemplary publications disclosing assays for assessing the level of ADCC induced by a protein include Hellstrom, et al. *Proc. Natl Acad. Sci. USA* 83:7059-7063, 1986 and Bruggemann, et al., *J. Exp. Med.* 166:1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

C1q binding assays may also be carried out to confirm that the protein is able to bind C1q and may induce CDC. To assess complement activation, a CDC assay may be performed (see, for example, Gazzano-Santoro et al, *J. Immunol. Methods* 202: 163, 1996.

Determining Half Life

Some proteins encompassed by the present disclosure have an improved half-life, e.g., are modified to extend their half-life compared to proteins that are unmodified. Methods for determining a protein with an improved half-life will be apparent to the skilled person. For example, the ability of a protein to bind to a neonatal Fc receptor (FcRn) is assessed. In this regard, increased binding affinity for FcRn increased the serum half-life of the molecule (see for example, Kim et al., *Eur J Immunol.*, 24:2429, 1994).

The half-life of a protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Therapeutic Efficacy

The efficacy of a compound to treat ischemia-reperfusion injury can be assessed using an in vivo assay. For example, by using a mouse model as described in Bohl et al., *Am J Physiol Heart Circ Physiol* (2009), Hartsock et al., *J Vis Exp* (2016), Greenberg et al., *Methods Enzymol* (2008), or Zhang et al., *The FASEB Journal* (2016).

Compositions

In some examples, a compound as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing a compound into a suitable form for administration (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or subcutaneous administration or administration into a body cavity or lumen of an organ or joint. The compositions for administration will commonly comprise a solution of the compound that inhibits G-CSF signaling dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compound of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, compounds of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

WO2002/080967 describes compositions and methods for administering aerosolized compositions comprising antibodies for the treatment of, e.g., asthma, which are also suitable for administration of a protein of the present disclosure.

Combination Therapies

In one example, a compound of the present disclosure is administered in combination with another compound useful for treating a disease or condition described herein, either as combined or additional treatment steps or as additional components of a therapeutic formulation.

For example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is methotrexate. Alternatively, or additionally, the other compound is cyclophosphamide. Alternatively, or additionally, the other compound is mycophenolate mofetil. Alternately or additionally the other compound is tissue plasminogen activator (t-PA).

In some examples, the other compound inhibits or reduces the expression or activity of one or more of:
(i) kidney injury molecule 1 (KIM-1);
(ii) neutrophil gelatinase-associated lipocalin (NGAL);
(iii) interleukin 1 beta (IL-1β);
(iv) interleukin 6 (IL-6);
(v) tumor necrosis factor alpha (TNFα);
(vi) complement component 5a receptor 1 (C5AR1);
(vii) macrophage inflammatory protein 2-alpha (MIP2-alpha);
(viii) intercellular Adhesion Molecule 1 (ICAM-1);
(ix) E-selectin;
(x) C-X-C motif chemokine ligand 1 (CXCL1);
(xi) interleukin 8 receptor beta (IL-8Rβ); and
(xii) monocyte chemoattractant protein 1 (MCP-1).

In some examples, the other compound is hydrogen sulfide. In some examples, the other compound is cyclosporine. In some examples, the other compound is TRO40303, as described in Le Lamer et al., *J Transl Med* (2014). In some examples, the other compound is superoxide dismutase. In some examples, the other compound is a cannabinoid or a synthetic analog thereof.

In some examples, the other compound is one that is commonly used in transplantation surgery.

In one example, the compound that inhibits G-CSF signaling is administered simultaneously with the other compound. In one example, the compound that inhibits G-CSF signaling is administered before the other compound. In one example, the compound that inhibits G-CSF signaling is administered after the other compound.

In some examples, the compound that inhibits G-CSF signaling is administered in combination with a cell. In some examples, the cell is a stem cell, such as a mesenchymal stem cell.

In some examples, the compound that inhibits G-CSF signaling is administered in combination with a gene therapy.

Dosages and Timing of Administration

Suitable dosages of compounds of the present disclosure will vary depending on the specific compound, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

In some examples, the compound that inhibits G-CSF signaling is administered systemically. In some examples, the compound that inhibits G-CSF signaling is administered locally.

It will be appreciated by those skilled in the art that in order to prevent or treat ischemia-reperfusion injury in a subject, the compound that inhibits G-CSF signaling is not necessarily directly administered to the subject. For instance, the compound may be administered to an organ donor or to an organ (e.g. a harvested organ) prior to transplantation to the subject, which thereby reduces the effects of the resulting ischemia-reperfusion injury in the subject after transplantation. Thus, ischemia-reperfusion injury in a subject can be treated without directly administering to the subject the compound that inhibits G-CSF signaling.

In some examples, the compound that inhibits G-CSF signaling is administered to the subject. In some examples, the subject is an organ transplant recipient.

In some examples, a method of the present disclosure comprises administering a prophylactically or therapeutically effective amount of a compound described herein.

The term "therapeutically effective amount" is the quantity which, when administered, improves the prognosis and/or state of the subject and/or that reduces or inhibits one or more symptoms of a clinical condition described herein to a level that is below that observed and accepted as clinically diagnostic or clinically characteristic of that condition. The amount to be administered will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of compound, rather the present disclosure encompasses any amount of the compound that inhibits G-CSF signaling sufficient to achieve the stated result in a subject. In one example, a therapeutically effective amount of the compound that inhibits G-CSF signaling does not induce neutropenia.

As used herein, the term "prophylactically effective amount" shall be taken to mean a sufficient quantity of a compound to prevent or inhibit or delay the onset of one or more detectable symptoms of a clinical condition. The skilled artisan will be aware that such an amount will vary depending on, for example, the specific compound administered and/or the particular subject and/or the type or severity or level of condition and/or predisposition (genetic or otherwise) to the condition. Accordingly, this term is not to be construed to limit the present disclosure to a specific quantity, e.g., weight or amount of compound, rather the present disclosure encompasses any amount of the compound that inhibits G-CSF signaling sufficient to achieve the stated result in a subject. In one example, a prophylactically effective amount of the compound that inhibits G-CSF signaling does not induce neutropenia.

For in vivo administration of the compounds described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In some examples, the compound that inhibits G-CSF signaling is administered at an initial (or loading) dose of between about 0.1 mg/kg to about 30 mg/kg, such as from about 1 mg/kg to about 10 mg/kg, or about 2 mg/kg to 8 mg/kg, or about 4 mg/kg to 6 mg/kg. The compound that inhibits G-CSF signaling can then be administered at a lower maintenance dose of between about 0.01 mg/kg to about 5 mg/kg, such as from about 0.05 mg/kg to about 1 mg/kg, for example, from about 0.1 mg/kg to about 1 mg/kg, such as about 0.1 mg/kg or 0.5 mg/kg or 1 mg/kg or 2 mg/kg or 3 mg/kg or 4 mg/kg or 5 mg/kg. The maintenance doses may be administered every 7-30 days, such as, every 10-15 days, for example, every 10 or 11 or 12 or 13 or 14 or 15 days. In this regard, a maintenance dose can be used in order to maintain a therapeutically effective level of the compound in the blood of the subject for a length of time, for example after organ transplantation surgery.

In some examples, the compound that inhibits G-CSF signaling is administered at a dose of between about 0.1 mg/kg to about 1 mg/kg. In some examples, the compound that inhibits G-CSF signaling is administered at a dose of between about 0.4 mg/kg to about 0.5 mg/kg. In one example, the compound that inhibits G-CSF signaling is administered at a dose of about 0.1 mg/kg. In one example, the compound that inhibits G-CSF signaling is administered at a dose of about 0.2 mg/kg. In one example, the compound that inhibits G-CSF signaling is administered at a dose of about 0.3 mg/kg. In one example, the compound that inhibits G-CSF signaling is administered at a dose of about 0.4 mg/kg. In one example, the compound that inhibits G-CSF signaling is administered at a dose of about 0.5 mg/kg. In one example, the compound that inhibits G-CSF signaling is administered at a dose of about 0.6 mg/kg. In one example, the compound that inhibits G-CSF signaling is administered at a dose of about 0.7 mg/kg. In one example, the compound that inhibits G-CSF signaling is administered at a dose of about 0.8 mg/kg. In one example, the compound that inhibits G-CSF signaling is administered at a dose of about 1 mg/kg.

In some examples, the compound that inhibits G-CSF signaling is administered at a dose of between about 0.01 mg/kg to about 50 mg/kg, such as between about 0.1 mg/kg to about 40 mg/kg, for example, between about 2 mg/kg to about 30 mg/kg, for example, between about 5 mg/kg to about 25 mg/kg.

In some examples, the compound that inhibits G-CSF signaling is administered at a dose of between about 2 mg/kg to about 8 mg/kg. In one example, the compound that inhibits G-CSF signaling is administered at a dose of between about 4 mg/kg to about 6 mg/kg.

In some examples, the compound that inhibits G-CSF signaling is administered at a dose of between about 10 mg/kg to about 40 mg/kg. In one example, the compound that inhibits G-CSF signaling is administered at a dose of between about 20 mg/kg to about 30 mg/kg.

In some examples, the compound that inhibits G-CSF signaling is administered at a dose of about 5 mg/kg. In some examples the compound that inhibits G-CSF signaling is administered at a dose of about 10 mg/kg. In some examples the compound that inhibits G-CSF signaling is administered at a dose of about 25 mg/kg.

In some examples, the compound that inhibits G-CSF signaling is administered without a higher loading dose or a lower maintenance dose.

In some examples, the compound that inhibits G-CSF signaling is administered as a single dose.

In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the compound that inhibits G-CSF signaling is administered every 7 days or every 14 days or every 21 days.

In some examples, at the time of commencing therapy, the mammal is administered the compound that inhibits G-CSF signaling on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Administration of a compound according to the methods of the present disclosure can be continuous or intermittent, depending, for example, on the recipient's physiological condition, whether the purpose of the administration is therapeutic or prophylactic, and other factors known to skilled practitioners. The administration of a compound may be essentially continuous over a preselected period of time or may be in a series of spaced doses, e.g., either during or after development of a condition.

In some examples, the compound that inhibits G-CSF signaling is administered before an ischemia. Thus, in some examples, the compound that inhibits G-CSF signaling is administered between between 0 days (e.g., immediately prior to ischemia) to 7 days before ischemia. For example, the compound that inhibits G-CSF signaling is administered between 0 days and 6 days or 5 days or 4 days before ischemia. For example, the compound that inhibits G-CSF signaling is administered between 0 and 48 hours before the ischemia. In some examples, the compound that inhibits G-CSF signaling is administered between 12 and 36 hours before the ischemia. In some examples, the compound that inhibits G-CSF signaling is administered about 24 hours before the ischemia. In other examples, the compound that inhibits G-CSF signaling is administered after the ischemia. In some examples, the compound that inhibits G-CSF signaling is administered before and after the ischemia. In some examples, the compound that inhibits G-CSF signaling is administered during the ischemia, for example during tissue or organ transplantation surgery.

In some examples, the compound that inhibits G-CSF signaling is administered at least 1 hour before the ischemia (e.g., out to 7 days or longer before ischemia). In some examples, the compound that inhibits G-CSF signaling is administered at least 2 or at least 4 or at least 6 or at least 8 or at least 10 or at least 12 hours or at least 14 hours or at least 16 hours or at least 18 hours or at least 20 hours or at least 22 hours or at least 24 hours before the ischemia.

In some examples, the compound that inhibits G-CSF signaling is administered before reperfusion. Thus, in some examples, the compound that inhibits G-CSF signaling is administered between between 0 days (e.g., immediately reperfusion) to 7 days before reperfusion. For example, the compound that inhibits G-CSF signaling is administered between 0 days and 6 days or 5 days or 4 days before reperfusion. For example, the compound that inhibits G-CSF signaling is administered between 0 and 48 hours before reperfusion. In some examples, the compound that inhibits G-CSF signaling is administered between 12 and 36 hours before reperfusion. In some examples, the compound that inhibits G-CSF signaling is administered about 24 hours before reperfusion. In other examples, the compound that inhibits G-CSF signaling is administered after reperfusion. In some examples, the compound that inhibits G-CSF signaling is administered before and after reperfusion.

In some examples, the compound that inhibits G-CSF signaling is administered at least 1 hour before reperfusion. In some examples, the compound that inhibits G-CSF signaling is administered at least 2 or at least 4 or at least 6 or at least 8 or at least 10 or at least 12 hours or at least 14 hours or at least 16 hours or at least 18 hours or at least 20 hours or at least 22 hours or at least 24 hours (e.g., out to 7 days or longer) before reperfusion.

Tissue or Organ Transplantation

When the ischemia-reperfusion injury is due to or associated with tissue or organ transplantation, the compound that inhibits G-CSF signaling can be administered either before, during or after transplantation. Thus, in some examples the compound that inhibits G-CSF signaling is administered before transplantation. In some examples the compound that inhibits G-CSF signaling is administered during transplantation, for example prior to clamp release at which time blood flow is restored to the transplanted organ. In some examples, the compound that inhibits G-CSF signaling is administered after transplantation.

In some examples, the compound that inhibits G-CSF signaling is administered to the subject, wherein the subject is a tissue or organ transplantation recipient. In some examples, the compound that inhibits G-CSF signaling is administered to the tissue or organ transplantation recipient before reperfusion. In one example, the compound that inhibits G-CSF signaling is administered to the tissue or organ transplantation recipient after reperfusion.

In some examples, the compound that inhibits G-CSF signaling is administered to the tissue or organ transplantation donor prior to tissue or organ harvest.

In some examples, the tissue or organ transplantation donor is a living donor. In some examples, the donor is a deceased donor. Deceased donors can be classified into several groups depending on the quality of the organ and/or the sequence and mechanisms of cessation of circulatory and respiratory functions. Classification of deceased donors is described in Panduranga & Akinlolu (Clin J Am Soc Nephrol 4: 1827-1831, 200).

In some examples, the donor is a donation after brain death (DBD) donor, also referred to as a 'brain-dead' donor. A DBD donor is a donor who has had primary brain death but whose circulatory system remains functional, either naturally or by medical measures (e.g., mechanical ventilation, drugs, intra-aortic balloon pump, or extracorporeal machine oxygenation device). In some examples, the compound that inhibits G-CSF signaling is administered to the DBD donor before organ harvest and is distributed to the potential transplant organs by blood circulation.

In some examples, the donor is a donation after circulatory death (DCD) donor, also referred to as a 'donation after cardiac death' donor or a 'non-heart-beating donor'. A DCD donor is a donor whose circulatory function had been lost (e.g., heart death) prior to organ harvest. In some examples, artificial circulation such as by heart-lung bypass instruments may be needed to deliver the compound administered to the DCD donor to the organ(s) contemplated for harvest and transplant. DCD donors can be further classified into further subgroups. In some examples the DCD donor is a controlled DCD (cDCD) donor. A cDCD donor is a donor whose life support will be withdrawn and whose family has given written consent for organ donation in the controlled environment of the operating room. In some examples, the DCD donor is an uncontrolled DCD (uDCD) donor. A uDCD donor is a donor, for example, who expires in the emergency room or elsewhere in the hospital before consent for organ donation is obtained and catheters are placed in the femoral vessels and peritoneum to cool organs until consent can be obtained. A uDCD donor is also a donor who has consented for organ donation but suffers a cardiac arrest requiring CPR during procurement of the organs.

In some examples, the donor is an expanded-criteria donor (ECD). An ECD is a donor who, at the time of death, is aged 60 or older or who is aged 50 to 59 years and has any two the following three criteria: (1) cause of death is cerebrovascular accident; (2) preexisting history of systemic hypertension; and (3) terminal serum creatinine greater than 1.5 mg/dL.

In some examples, the donor is a standard-criteria donor (SCD). A SCD is a donor who is less than 50 years in age. Generally, all deceased donors for whom donation occurred after brain death and who do not meet any of the criteria for an ECD (see above) are considered an SCD.

In some examples, the compound that inhibits G-CSF signaling is administered shortly following determination of brain death, or as soon following brain death as is feasible given legal, ethical, and patient considerations. The attendant physician or transplant surgeon will recognise a multiplicity of factors that influence the timing of organ harvest from a suitable donor and transplant of harvested organs into a suitable recipient. Thus, in some examples, the compound that inhibits G-CSF signaling is administered to the donor at any time between the occurrence of brain death and removal of an organ intended for transplant.

In some examples, the compound that inhibits G-CSF signaling is administered to a harvested tissue or organ ex vivo, prior to tissue or organ transplantation. For example, the harvested tissue or organ can be perfused or infused with a solution comprising the compound that inhibits G-CSF signaling prior to transplantation.

Kits

Another example of the disclosure provides kits containing compounds useful for the treatment of ischemia-reperfusion injury as described above.

In one example, the kit comprises (a) a container comprising a compound that inhibits G-CSF signaling as described herein, optionally in a pharmaceutically acceptable carrier or diluent; and (b) a package insert with instructions for reducing an effect of ischemia-reperfusion injury in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the ischemia-reperfusion injury and may have a sterile access port (for example, the container may be an intravenous solution bag or a vial having a stopper pierceable by a hypodermic injection needle). At least one active agent in the composition is the compound that inhibits G-CSF signaling that inhibits G-CSF signaling. The label or package insert indicates that the composition is used for treating a subject eligible for treatment, e.g., an organ transplant recipient, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The present disclosure includes the following non-limiting Examples.

EXAMPLES

Example 1: Methods and Materials

Mice

Adult male C57BL/6 wild type mice aged 10 to 12 weeks were obtained from the Animal Resource Centre, Perth, Australia. Mice were housed in an approved animal facility within St. Vincent's Hospital Melbourne, and all experiments involving animals were approved by the Animal Ethics Committee of St. Vincent's Hospital Melbourne.

Warm Renal Ischemia-Reperfusion Injury Model

Mice were anesthetized by i.p. administration of ketamine 85 mg/kg and xylazine 15 mg/kg. After the mice were anesthetized, they were placed on a heating pad to maintain their core body temperature at 37° C. during the surgery. A midline abdominal incision was made and the renal pedicles were bluntly dissected. After right nephrectomy, a microvascular clamp (Roboz, Rockville, MD) was placed on the left renal pedicle for 22 min, while the animal was kept at 37° C. in an incubator and well hydrated. The clamp was removed after ischemia and the kidney observed to confirm complete reperfusion. The surgical wounds were then sutured in two layers with 5-0 silk. Warm normal saline (100 ml/kg) was instilled into the peritoneal cavity during the procedure. The mice were allowed to recover for 2 h under a heating lamp and then kept on a heating pad. The mice were euthanized 24 h after reperfusion, and blood and kidney samples obtained. Sham-operated mice had right nephrectomy only, without IR.

Antibodies

Anti-mouse G-CSFR (Ch5E2-VR81-mIgG1κ), isotype control (BM4, mouse isotype IgG1κ) or anti-C5 antibody (muBB5.1-mIgG1κ) (Rother R, et al. *Nat Biotechnol.* 2007) were injected at 100 μg/mouse in 0.2 ml PBS intraperitoneally 24 h before starting ischemia. In a dose titration study, anti-mouse G-CSFR (Ch5E2-VR81-mIgG1κ) was injected at 200 μg/mouse or 500 μg/mouse in 0.2 ml PBS intraperitoneally 24 h before ischemia. Isotype control was injected at the highest dose, so 500 μg/mouse. VR81 is a mouse monoclonal IgG1K antibody produced against the extracellular domain of murine G-CSFR and blocks G-CSF binding to G-CSFR as described (Campbell et al. *Journal of Immunology*, 197(11) (2016) 4392-4402). In this regard, VR81 is mouse surrogate antibody for C1.2 and C1.2G described herein and in WO2012171057.

Assessment of Renal Function

Renal function was assessed by measurement of serum creatinine and serum or plasma urea at 24 hours after reperfusion. Creatinine was measured using a kinetic colorimetric assay based on the Jaffé method, analyzed on a Roche COBAS Integra 400 Plus analyzer. Cell Biolabs' Urea Assay Kit is based on the Berthelot reaction. Urea is first degraded into ammonia and carbon dioxide, which further reacts with an alkaline developer to produce a blue-green colored product that can be measured with a standard spectrophotometric plate reader at an optical density between 580-630 nm.

Renal Histology and Scoring

Kidney tissue sections (4 mm) were 10% formalin fixed and paraffin embedded then stained with H&E. Histology scores were assessed by a semi-quantitative method (Lu B et al. *Nephrology* 2008). Briefly, three high-power fields in each of the cortex, cortical-medullary junction, and medulla in a minimum of two sections were assessed in a blinded fashion. The degree of tubular necrosis was graded and a modified scoring system was used: 0=normal kidney; 1=minimal (#10% involvement); 2=mild (10-25% involvement); 3=moderate (26-50% involvement); 4=severe (51-75% involvement); and 5=very severe (0.75% involvement).

Complement Activation and Deposition

The activation of complement in mouse plasma was measured using a mouse C5a DuoSet ELISA kit (DY2150; R&D Systems, Minneapolis, MN) according to the manufacturer's instructions. Deposition of the C5b-9 in kidney sections was measured by immunofluorescence (see below).

Immunofluorescence

Snap-frozen biopsy samples were cut into 5-mm-thick sections, air dried, and either processed immediately or stored at 280° C. until further analysis. After fixation with acetone and hydration, the sections were stained using: rabbit anti-mouse C9 Alexa 488 (Bioss Antibodies, Woburn, MA), rat anti-mouse Ly-6GFITC (Hycult Bio-tech), rat anti-mouse F4/80 FITC (Bio-Rad, Raleigh, NC), or FITC-conjugated isotype-matched control Ab: rat IgG1 (BD Biosciences, San Diego, CA). The slides were analyzed using a fluorescence/confocal microscope (Nikon AiR). Quantification of fluorescence intensity as raw integrated density was performed using ImageJ software, version 10.2 (National Institutes of Health) on unmanipulated TIFF images.

RNA Extraction, Complementary DNA Synthesis, and Quantitative Real-Time Polymerase Chain Reaction Total RNA from frozen mouse kidneys was isolated using the PureLink RNA mini kit (Life Technologies, Carlsbad, CA) according to the manufacturer's instructions. Total RNA quality and quantity were determined using the NanoDrop spectrophotometer (NanoDrop Technologies, Oxfordshire, UK). First-strand complementary DNA synthesis was performed by incubating 1.0 μg total RNA in a 50-μL reaction mix containing 0.5 μg Oligo (dT) primers and 1 μg random primers (both from Invitrogen, Carlsbad, CA) at 70° C. for 10 minutes. A 50-μL reaction mix containing 10 mM dNTP, 300 U SuperScript III recombinant ribonuclease inhibitor, 60 U RNaseOUT recombinant ribonuclease inhibitor, 0.1 M DTT, and 5 first-strand buffer (all from Invitrogen) was then added. Reverse transcription was performed at 42° C. for 1 hour and 70° C. for 10 minutes. The complementary DNA was stored at −20° C. Real-time polymerase chain reaction was performed using the TaqMan Universal PCR Master Mix system according to the manufacturer's instructions (Applied Biosystem, Bedford, MA).

Kidney Digestion and Peripheral Blood Preparation

A ⅛ piece of kidney was cut with a scalpel into smaller pieces, which were digested in 500 ul Collagenase Type I (10 ug/ml in PBS 2 mM EDTA) under shaking conditions at 37° C. for 30 min. Cells were isolated by passing the tissue digest through a 70 um strainer. Red blood cells were lysed using RCRB buffer (156 mM NH4Cl, 11.9 mM NaHCO$_3$, 0.097 mM EDTA, pH7.3). Cells were finally resuspended in PBS 2 mM EDTA.

Peripheral blood was collected into EDTA-coated tubes, red blood cells were lysed using RCRB buffer (as above) and cells were resuspended in PBS 2 mM EDTA.

Flow Cytometry

Single-cell suspensions of kidney and peripheral blood were resuspended in PBS with 2 mM EDTA. Cells were stained with the following Ab's: PE-conjugated anti-mouse Gr-1 (R86-8C5; BD Biosciences), allophycocyanin Cy7-conjugated anti-mouse Ly6G (1A8; BD Biosciences), FITC-conjugated anti-mouse CD11b (M1/70; BD Biosciences), PECy7-conjugated anti-mouse CD69 (H1.2F3; BD Biosciences), eFluor450-conjugated anti-mouse CD62L (MEL-14; eBiosecience), allophycocyanin-conjugated anti-mouse CD45.2 (104; eBiosciences). FcR block anti-mouse CD16/32 (93; Biolegend) was added to reduce non-specific binding and Fixable Live/Dead Yellow (Thermo Fisher Scientific) was used to exclude dead cells. Samples were fixed overnight using BD Cytofix Fixation buffer (BD Biosciences) and then analysed on a BD Fortessa, using FlowJo software.

Statistical Analysis

Statistical tests were performed using GraphPad Prism software. Multiple groups were compared using one-way ANOVA with a post-test Bonferroni correction or a Kruskal-Wallis test with Dunn's multiple comparison test. Two groups were compared using an unpaired Student t test (two-tailed) or a Mann-Whitney U test. Results are expressed as mean±SEM. A p value<0.05 was considered to be statistically significant.

Example 2: Inhibition of G-CSF Signaling in a Warm Renal IRI Model Reduces Serum Creatinine and Plasma Urea Concentrations To assess whether inhibition of G-CSF signaling in mice subjected to warm renal ischemia-reperfusion injury (IRI)

reduces renal injury, analysis of serum creatinine and plasma/serum urea concentrations was performed.

Significant reduction in serum creatinine concentrations was seen in mice treated with 100 µg of an anti-G-CSFR antibody (VR81) (n=8; mean±SEM; 66.13±25.18) compared to serum creatinine concentrations in mice treated with 100 µg of an isotype control antibody (n=8; mean±SEM; 134.38±20.57) (FIG. 1, Table 1).

Figure 2:
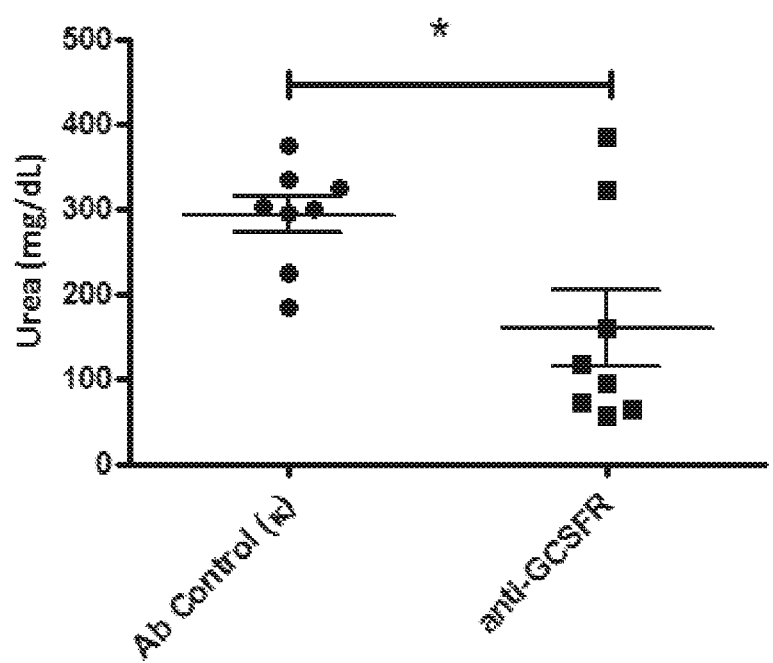
FIG. 2 is a graphical representation of plasma urea concentrations 24 hours post reperfusion in the renal warm ischemia-reperfusion injury model. Treatment of mice with 100 μg of the anti-G-CSFR antibody VR81 significantly reduced plasma urea concentrations compared to treatment of mice with 100 μg of an isotype control antibody. Unpaired T-test *$p<0.05$ ($n=8$ mice per group). The results are representative of two independent experiments—see also FIG. 8.
Figure 9:
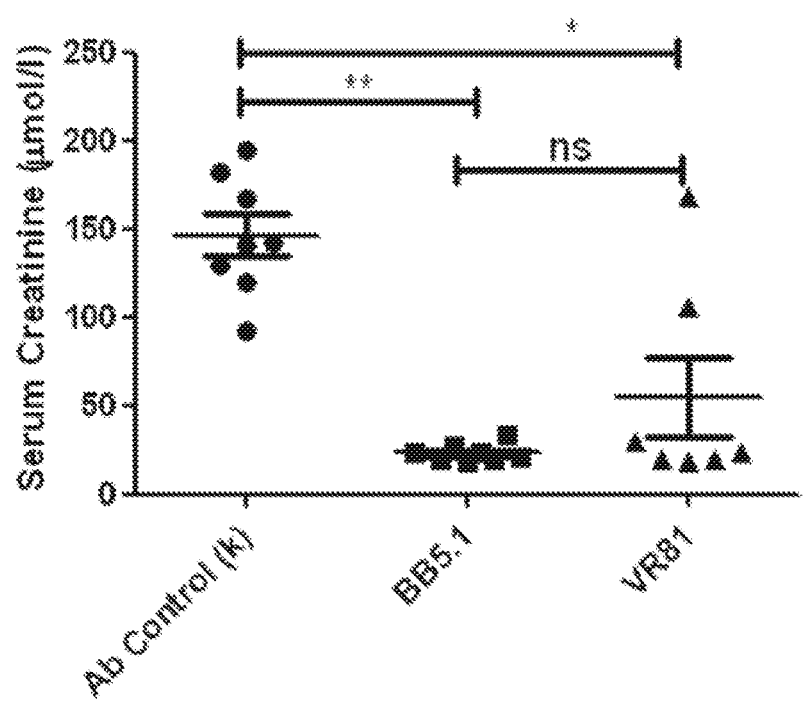
FIG. 9 is a graphical representation of serum creatinine concentrations in the warm renal IRI model. Treatment with 100 μg of the anti-G-CSFR antibody VR81 or 100 μg of the anti-C5 antibody BB5.1 significantly reduced creatinine concentrations compared to treatment of mice with 100 μg of an isotype control antibody. The reductions seen with the VR81 and with BB5.1 were not significantly different. One-Way ANOVA Kruskal-Wallis test, Dunn's Multiple Comparison Test, *$p<0.05$, $p<0.01$, *$p<0.005$ ($n=7$-$8$ mice per group).
Figure 10:
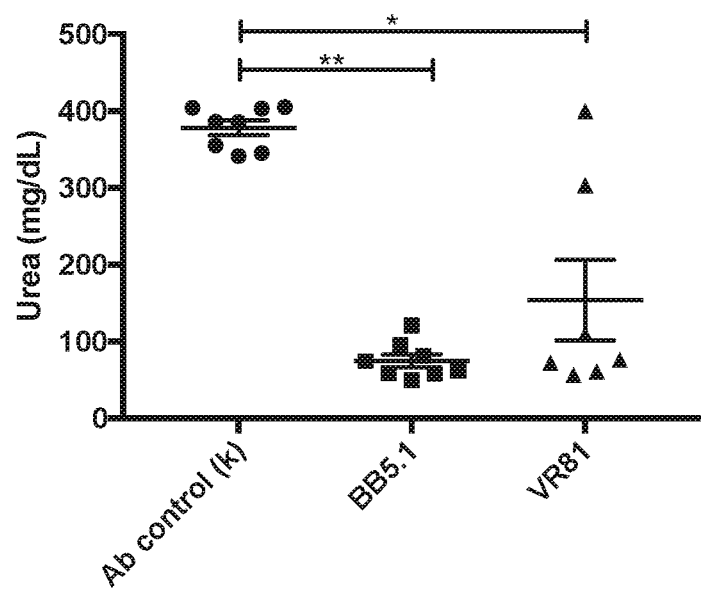
FIG. 10 is a graphical representation of plasma urea concentrations in the warm renal IRI model. Treatment with 100 μg of the anti-G-CSFR antibody VR81 or 100 μg of the anti-C5 antibody BB5.1 significantly reduced plasma urea concentrations compared to treatment of mice with 100 μg of an isotype control antibody. The reductions seen with VR81 and with BB5.1 were not significantly different. One-Way ANOVA Kruskal-Wallis test, Dunn's Multiple Comparison Test, *$p<0.05$, **$p<0.01$ ($n=7$-$8$ mice per group).

A significant reduction in plasma urea concentrations was observed in mice treated with an anti-G-CSFR antibody (VR81) (n=8; mean±SEM; 159.02±44.42) compared to an isotype control antibody (n=8; mean±SEM; 292.49±21.35) (FIG. 2, Table 1). The concentrations of serum creatinine and plasma urea in mice treated with an anti-G-CSFR antibody (VR81) prior to IRI were comparable to those seen in mice not subjected to treatment or surgery (sham) (FIGS. 1 and 2; Table 1). Furthermore, the concentrations of serum creatinine and plasma urea in mice treated with VR81 were not statistically different to those seen in mice treated with an anti-C5 antibody (BB5.1) (FIGS. 9 and 10).

TABLE 1

Serum creatinine and plasma urea levels in mice treated with 100 µg anti-G-CSFR antibody (VR81) or an isotype control antibody intraperitoneally (IP) - warm renal IRI model.

| Mouse number | Treatment Group | Serum Creatinine (µmol/l) | Plasma Urea (mg/dL) |
|---|---|---|---|
| 2276 | Isotype control | 183 | 324 |
| 2278 | Isotype control | 90 | 225 |
| 2279 | Isotype control | 208 | 373 |
| 2285 | Isotype control | 122 | 302 |
| 2286 | Isotype control | 85 | 295 |
| 2289 | Isotype control | 205 | 335 |
| 2290 | Isotype control | 55 | 185 |
| 2275 | Isotype control | 127 | 299 |
| 2277 | anti-G-CSFR (VR81) | 148 | 322 |
| 2280 | anti-G-CSFR (VR81) | 19 | 71 |
| 2281 | anti-G-CSFR (VR81) | 35 | 94 |
| 2282 | anti-G-CSFR (VR81) | 208 | 384 |
| 2283 | anti-G-CSFR (VR81) | 38 | 159 |
| 2284 | anti-G-CSFR (VR81) | 35 | 117 |
| 2287 | anti-G-CSFR (VR81) | 26 | 57 |
| 2288 | anti-G-CSFR (VR81) | 20 | 64 |

Example 3: Inhibition of G-CSF Signaling in a Warm Renal IRI Model Reduces Inflammatory Infiltration in the Renal Tissue To assess the effect of administration of anti-G-CSFR antibody (VR81) to mice subjected to warm renal ischemia-reperfusion injury (IRI), neutrophil and macrophage infiltration into renal tissue was measured by immunofluorescence microscopy according to Example 1.

Figure 3:
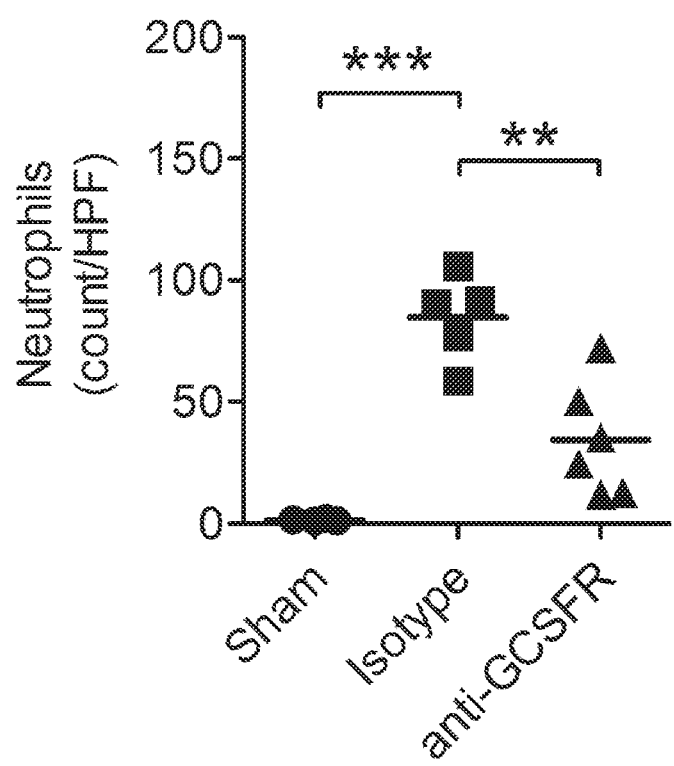
FIG. 3 is a graphical representation of neutrophil count per high power field (HPF) in renal tissue. Treatment of mice with 100 μg of the anti-G-CSFR antibody VR81 significantly reduced neutrophil renal infiltration in the warm renal IRI model compared to neutrophil infiltration seen in mice treated with 100 μg of an isotype control antibody as assessed 24 hours post-reperfusion. One-Way ANOVA (with Bonferroni correction), *$p<0.05$, $p<0.01$, *$p<0.005$ ($n=5$-$6$ mice per group).
Figure 4:
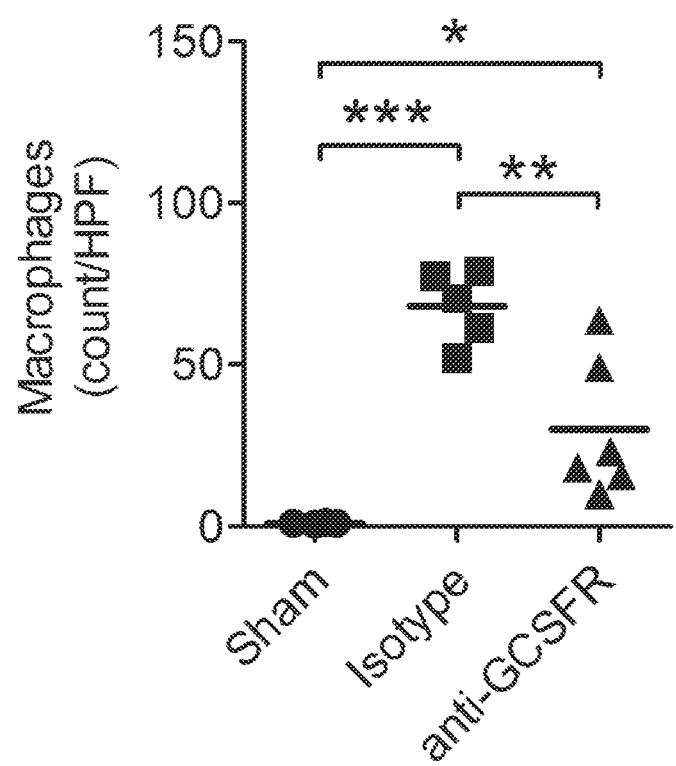
FIG. 4 is a graphical representation of macrophage count per high power field (HPF) in renal tissue. Treatment of mice with 100 μg of the anti-G-CSFR antibody VR81 significantly reduced macrophage renal infiltration in the warm renal IRI model compared to macrophage infiltration seen in mice treated with 100 μg of an isotype control antibody as assessed 24 hours post-reperfusion. One-Way ANOVA (with Bonferroni correction), *$p<0.05$, **$p<0.01$ ($n=5$-$6$ mice per group).

Infiltration of neutrophils and macrophages within the tubular interstitium at the corticomedullary junctions of the kidneys was significantly reduced in mice treated with 100 µg of anti-G-CSFR antibody (VR81) compared to mice treated with 100 µg of an isotype control antibody. Little/no infiltration was observed in the sham mice (FIGS. 3 and 4). One-Way ANOVA (with Bonferroni correction) was used for testing significance.

Figure 5A:
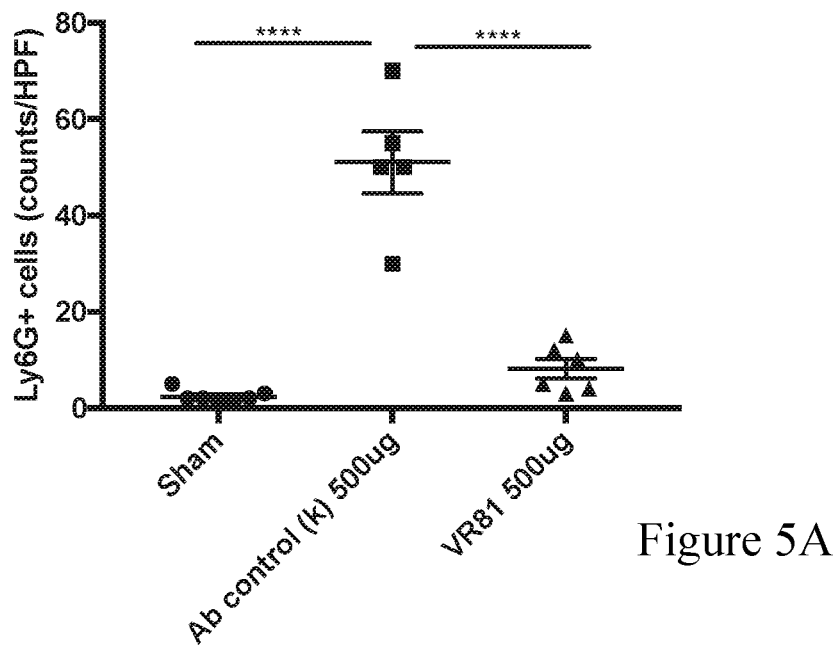
FIG. 5 is a graphical representation of (A) neutrophil and (B) macrophage count per high power field (HPF) in renal tissue. Treatment of mice with 500 μg of the anti-G-CSFR antibody VR81 significantly reduced neutrophil and macrophage renal infiltration in the warm renal IRI model compared to neutrophil infiltration seen in mice treated with 500 μg of an isotype control antibody as assessed 24 hours post-reperfusion. One-Way ANOVA (with Bonferroni correction), ****$p<0.0001$ ($n=5$-$6$ mice per group).
Figure 5B:
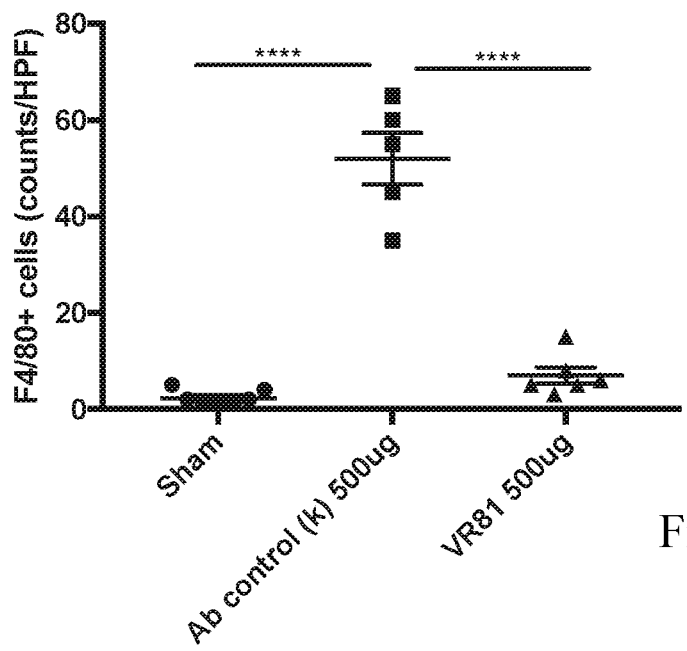

In a separate experiment, infiltration of neutrophils and macrophages was also significantly reduced in mice treated with 200 µg, and 500 µg of VR81 compared to mice treated with 500 µg of an isotype control antibody (Table 2 and FIG. 5).

TABLE 2

Reduction in neutrophil and macrophage infiltration within the tubular interstitium at the corticomedullary junctions of the kidneys D'Agostino & Pearson omnibus normality test. One-Way ANOVA Kruskal-Wallis test, Dunn's Multiple Comparison Test for VR81 vs Ab control (*p < 0.05, **p < 0.01).

| Treatment | Neutrophils (counts/HIPF) | Macrophages (counts/HPF) |
|---|---|---|
| Sham | 2.28 ± 0.52 | 2.29 ± 0.61 |
| Ab control (500 µg) | 51.0 ± 6.40 | 52.0 ± 3.38 |
| VR81 (200 µg) | 27.0 ± 5.15 | 20.0 ± 7.07 |
| VR81 (500 µg) | 8.17 ± 1.99** | 7.00 ± 1.73* |

Example 4: Inhibition of G-CSF Signaling in a Warm Renal IRI Model Reduces Necrosis in the Renal Cortex Kidney damage in the renal cortex was assessed in the warm renal IRI model in in mice treated with 100 µg of an anti-G-CSFR antibody (VR81). The degree of tubular necrosis was graded and expressed as a Tubular Injury (TI) score in accordance with Table 3. TI was determined without knowledge of the treatment group by two independent operators assessing the percentage of renal tubular injury involvement (necrosis, cast formation, cell swelling, and dilatation).

Figure 6:
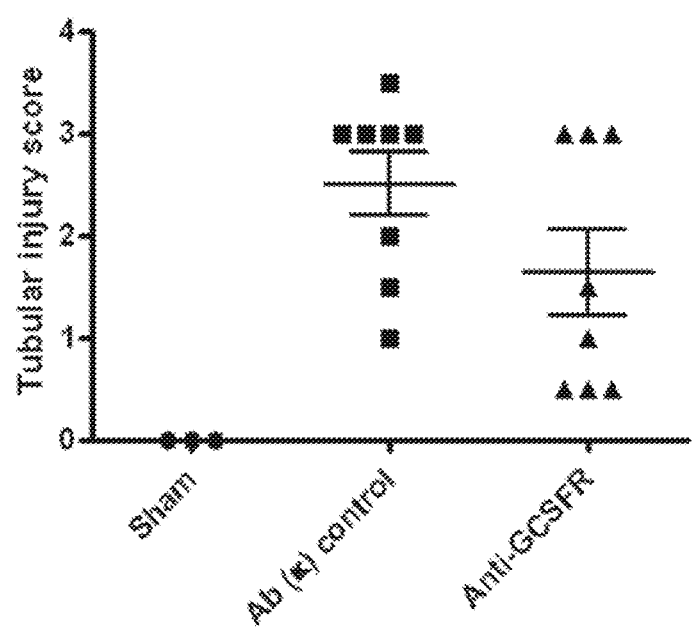
FIG. 6 is a graphical representation of renal tubular injury in the warm IRI model as determined by the degree of tubular necrosis observed in the renal cortex of treated mice (sham; 100 μg of the anti-G-CSFR antibody VR81; 100 μg of an isotype control antibody). Necrosis was assessed by a semiquantitative method (Lu B et al. Nephrology 2008) using fluorescence microscopy. The degree of tubular necrosis was graded and a modified scoring system was used (see Table 3). One-Way ANOVA Kruskal-Wallis test, Dunn's Multiple Comparison Test, *$p<0.05$, $p<0.01$, *$p<0.005$ ($n=8$ mice per group other than sham where $n=3$).

A trend of reduced tubular injury was observed in the kidneys of mice treated with the anti-G-CSFR antibody (VR81) (FIG. 6; mean of two independent assessments per mouse displayed). Sham mice displayed no tubular injury as expected.

TABLE 3

Reference table defining percentage of necrotic cells in the renal cortex and the corresponding tubular injury (TI) score.

| Tubular Injury (TI) score | % tubular necrosis (cortex only) |
|---|---|
| 0 | Normal |
| 1 | <10 |
| 2 | 10-25 |
| 3 | 26-50 |
| 4 | 51-75 |
| 5 | >75 |

Example 5: KIM-1, NGAL, IL-6, IL-8Rβ/CXCR2, MCP-1/CCL2, CXCL1, MIP-2/CXCL2, ICAM-1, and C5aR mRNA Expression in Renal Tissue—Warm Renal IRI Model In an initial experiment, mice were injected with 100 µg/mouse of the anti-G-CSFR antibody VR81 24 h before ischemia/reperfusion injury was induced in the warm renal IRI model. After reperfusion, RNA was isolated from the kidneys and subjected to qRT-PCR as described in Example 1. The mRNA transcript levels of KIM-1, NGAL, IL-6, IL-8Rβ/CXCR2, MCP-1/CCL2, ICAM-1, C5aR, IL-10, TNFα, CXCL1, MIP-2/CXCL2 and E-selectin were determined. Transcript levels of these genes were quantified and normalised against GAPDH.

Anti-G-CSFR antibody (VR81) treatment at a dosage of 100 µg/mouse 24 h reduced gene expression of NGAL, IL-6, IL-8Rβ/CXCR2, ICAM-1, C5aR, MIP-2/CXCL2, MCP-1/CCL2, E-selectin, and CXCL1 compared to treatment with the isotype control antibody. These data suggest that inhibition of G-CSF signaling is effective in reducing the inflammatory response associated with IRI. A similar pattern of reduced expression of the above genes was observed in the kidneys of mice treated with anti-C5 antibody (BB5.1).

Figure 7A:
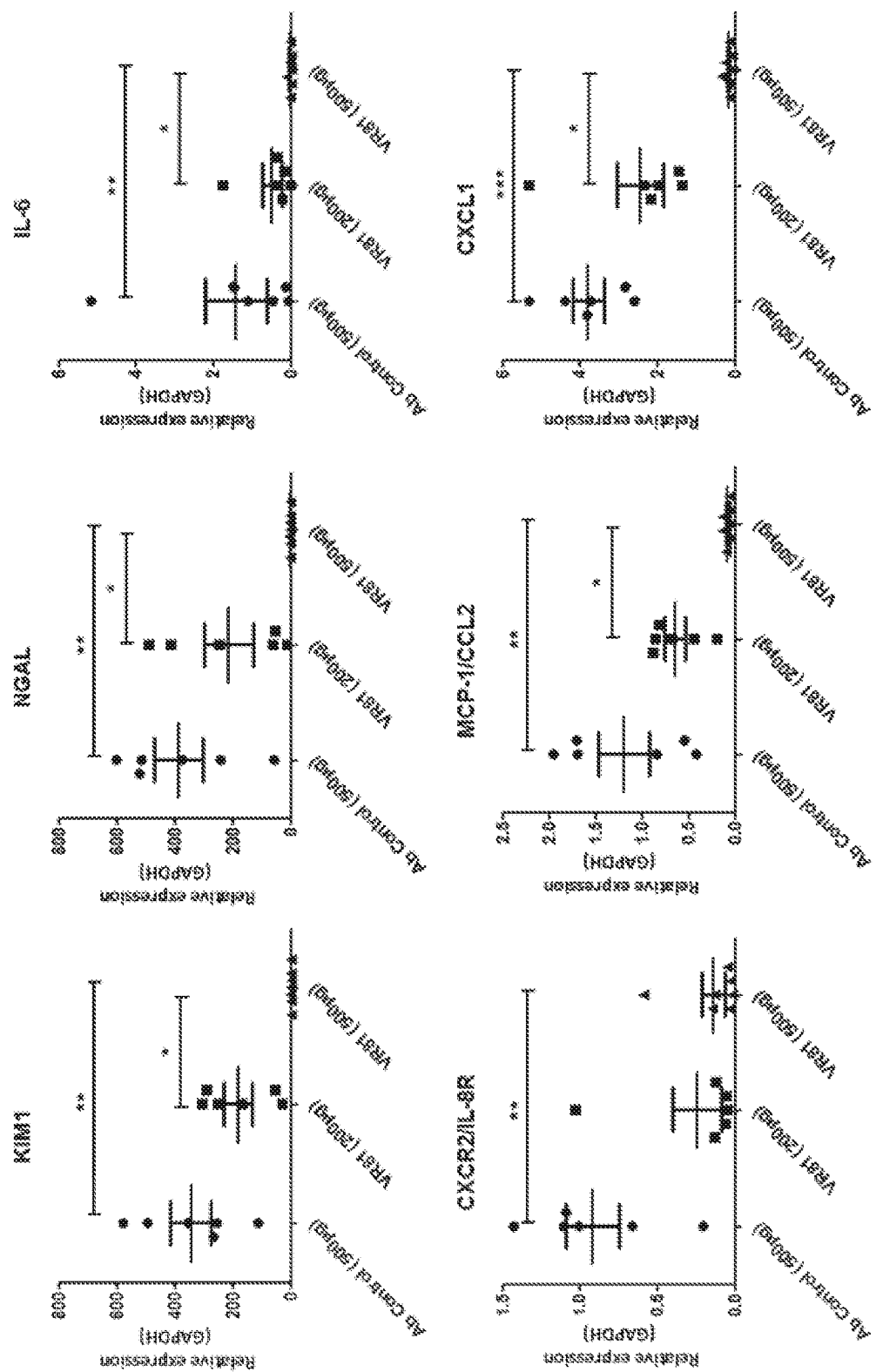
FIG. 7 is a graphical representation of KIM-1, NGAL, IL-6, IL-8Rβ/CXCR2, MCP-1/CCL2, CXCL1, MIP-2/CXCL2, ICAM-1, and C5aR mRNA expression in renal tissue in the warm renal IRI model as assessed by qRT-PCR. VR81 treatment at a dosage of 500 μg/mouse significantly reduced expression of (A) KIM-1, NGAL, IL-6, IL-8Rβ/CXCR2, MCP-1/CCL2, CXCL1, and (B) MIP-2/CXCL2, ICAM-1, and C5aR compared to treatment with the isotype control antibody. One-Way ANOVA Kruskal-Wallis test, Dunn's Multiple Comparison Test for VR81 vs Ab control * $p<0.05$,  $p<0.01$, * $p<0.005$.
Figure 7B:
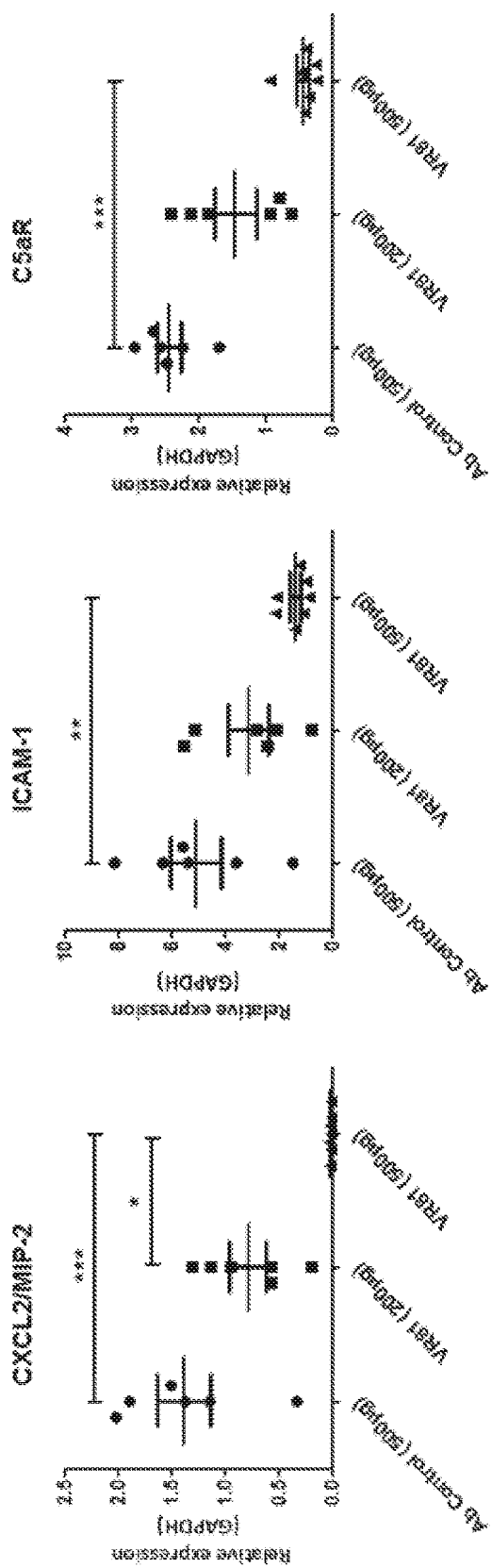

The initial results were confirmed using a dose of 200 μg/mouse or 500 μg/mouse of VR81. Table 4 and FIG. 7 shows that VR81 treatment at a dosage of 500 μg/mouse significantly reduced expression of KIM-1, NGAL, IL-6, IL-8Rβ/CXCR2, ICAM-1, C5aR, MIP-2/CXCL2, MCP-1/CCL2, and CXCL1 compared to treatment with the isotype control antibody.

No significant difference in the percentage of leukocytes (CD11b-Gr1-CD45.2$^+$) was observed in the kidneys of mice treated with anti-G-CSFR antibody (VR81) or anti-C5 antibody (BB5.1) compared to mice treated with an isotype control antibody.

Example 7: VR81 Dose Titration in the Warm Renal IRI Model

In a dose titration study in the warm renal IRI model described in Example 1, anti-mouse G-CSFR antibody (VR81) was injected 24 h before ischemia-reperfusion injury at a dose of 200 μg/mouse or 500 μg/mouse. Mice treated with 500 μg/mouse of the isotype control antibody served as controls.

TABLE 4

Relative expression of chemokine receptors and cytokines in renal tissue of mice dosed with 200 μg or 500 μg of VR81. D'Agostino & Pearson omnibus normality test. One-Way ANOVA Kruskal-Wallis test, Dunn's Multiple Comparison Test for VR81 vs Ab control (*p < 0.05, p < 0.01, *p < 0.005).

|  | KIM-1 | NGAL | IL-6 | CXCR2/IL-8R | MCP-1/CCL2 |
|---|---|---|---|---|---|
| Control (500 ug) | 343.4 ± 69.70 | 386 ± 83.32 | 1.42 ± 0.787 | 0.917 ± 0.173 | 1.195 ± 0.273 |
| VR81 (200 ug) | 183.3 ± 48.6† | 213.8 ± 83.03† | 0.488 ± 0.258† | 0.244 ± 0.159† | 0.650 ± 0.112† |
| VR81 (500 ug) | 0.271 ± 0.076** | 2.859 ± 0.583** | 0.0207 ± 0.015** | 0.141 ± 0.077** | 0.005 ± 0.016** |

|  | CXCL1 | MIP-2/CXCL2 | ICAM-1 | C5aR |
|---|---|---|---|---|
| Control (500 ug) | 3.786 ± 0.410 | 1.38 ± 0.249 | 5.09 ± 0.936 | 2.44 ± 0.176 |
| VR81 (200 ug) | 2.45 ± 0.597† | 0.788 ± 0.169† | 3.13 ± 0.748 | 1.45 ± 0.312 |
| VR81 (500 ug) | 0.168 ± 0.040*** | 0.016 ± 0.003*** | 1.40 ± 0.196** | 0.435 ± 0.089*** |

Example 6: Inhibition of G-CSF Signaling Reduces Neutrophil Infiltration into the Kidney in a Warm Renal IRI Model Kidney neutrophils (CD11b$^+$Gr1$^+$) and leukocytes (CD11b-Gr1-CD45.2$^+$) were enumerated by tissue digestion and flow cytometry according to the methods described in Example 1. The percentage of live cells was determined based on PI staining of total cell populations.

Figure 8A:
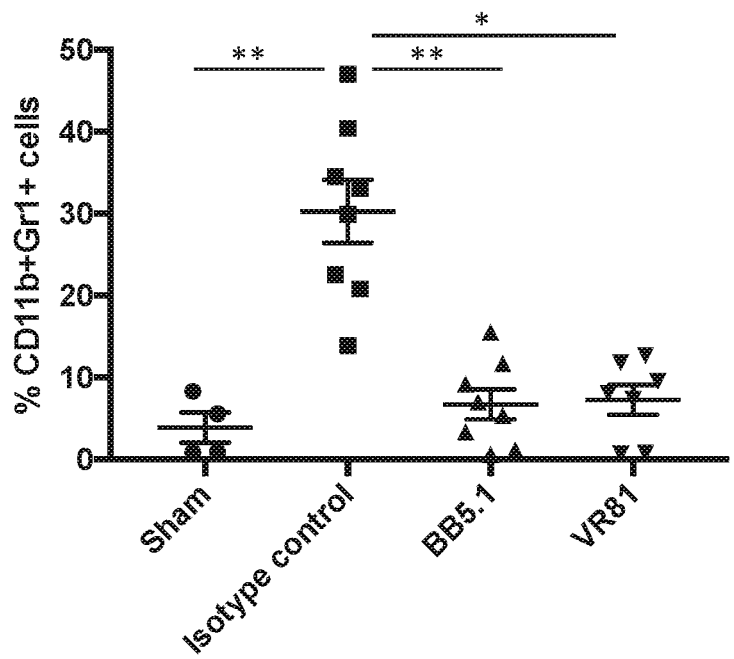
FIG. 8 is a graphical representation of the percent frequency of neutrophils (CD11b$^+$Gr1$^+$) in the warm renal IRI model as assessed by flow cytometry in (A) kidney and (B) peripheral blood of mice treated with 100 μg of the anti-G-CSFR antibody VR81 or 100 μg of an anti-C5 antibody (BB5.1) compared to mice treated with 100 μg of an isotype control antibody and sham mice. Significantly lower levels of neutrophils (CD11b$^+$Gr1$^+$) were observed in the kidneys of sham mice and mice treated with VR81 or BB5.1 compared to the levels observed in mice treated with an isotype control antibody. Neutrophil populations in the blood were similar in all groups and unaffected by the treatments. One-Way ANOVA Kruskal-Wallis test, Dunn's Multiple Comparison Test, *$p<0.05$, **$p<0.01$ ($n=7$-$8$ mice per group other than sham where $n=4$).
Figure 8B:
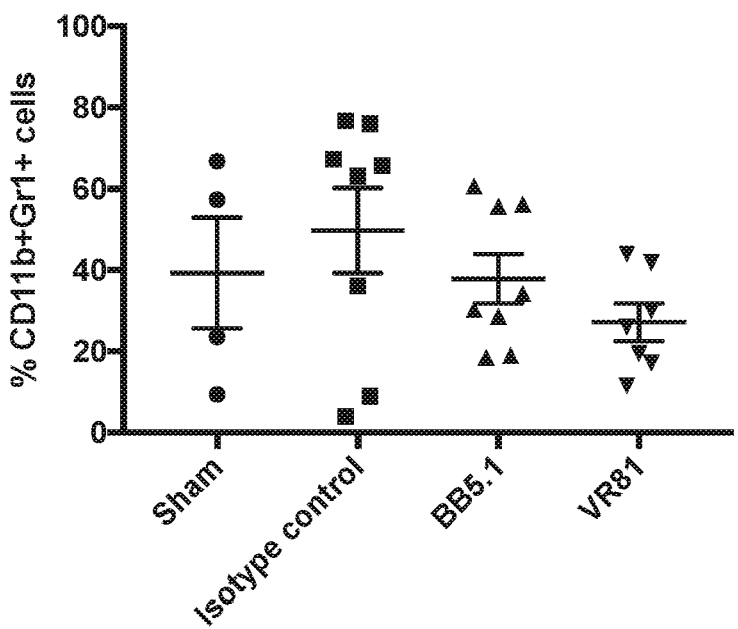

Reduced numbers of neutrophils were observed in the kidneys of mice treated with 100 μg/mouse of an anti-GCSFR antibody (VR81) or anti-C5 antibody (BB5.1) (and sham mice) compared to mice treated with an isotype control antibody (FIG. 8A). Peripheral blood neutrophil numbers were similar in all experimental groups (FIG. 8B).

Figure 13A:
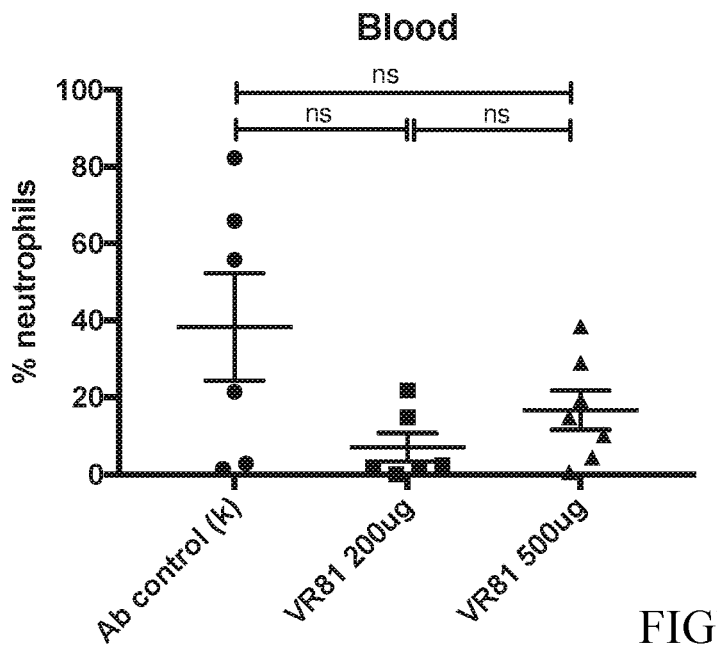
FIG. 13 is a graphical representation of the percent frequency of neutrophils (CD11b$^+$Gr1$^+$Ly6G+) in (A) blood and (B) kidney in the warm renal IRI model. Treatment with 200 μg/mouse and 500 μg/mouse of the anti-G-CSFR antibody VR81 significantly reduced the frequency of neutrophils in the kidney compared to treatment with 500 µg/mouse of an isotype control antibody. Stats: One-Way ANOVA (with Bonferroni correction), *p<0.05, **p<0.01 (n=6-7 mice per group).
Figure 13B:
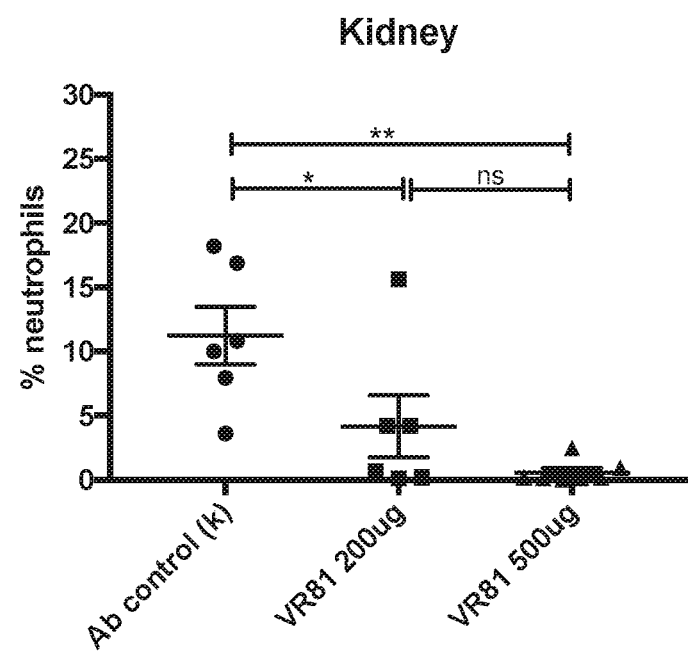

Similarly, there was a significant reduction in the numbers of neutrophils observed in the kidneys of mice treated with 200 μg/mouse or 500 μg/mouse of VR81 compared to mice treated with an isotype control antibody (FIG. 13A). However, there was not a significant reduction of neutrophils observed in peripheral blood, relative to the isotype control antibody (FIG. 13B).

These data suggest that treatment with anti-G-CSFR antibody (VR81) reduces neutrophil infiltration into the kidney and does not significantly impact on the numbers of neutrophils in the peripheral blood.

No significant difference was seen in the expression of CD69 or CD62L by neutrophils in the kidneys or peripheral blood across all experimental groups of mice.

Figure 11:
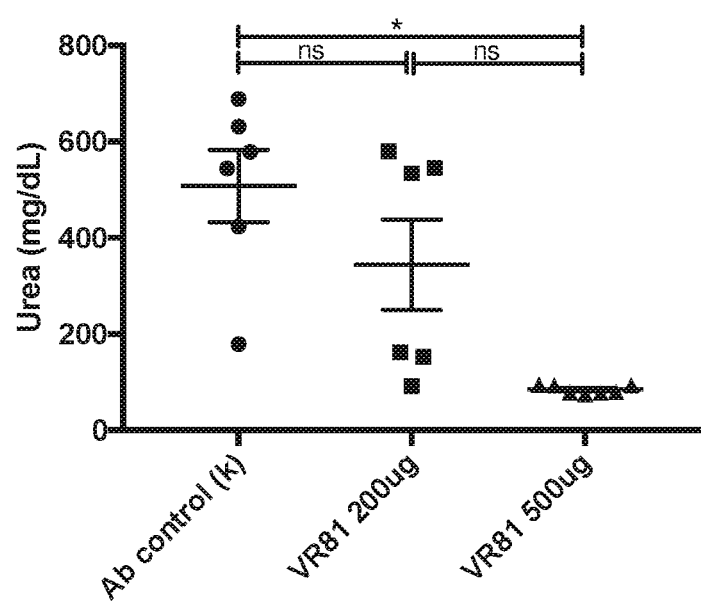
FIG. 11 is a graphical representation of serum urea concentrations in the warm renal IRI model. Treatment of mice with 500 μg of the anti-G-CSFR antibody VR81 significantly reduced serum urea concentrations compared to treatment of mice with 500 μg of an isotype control antibody. One-Way ANOVA Kruskal-Wallis test, Dunn's Multiple Comparison Test *$p<0.05$, **$p<0.01$ ($n=6$-$8$ mice per group).
Figure 12:
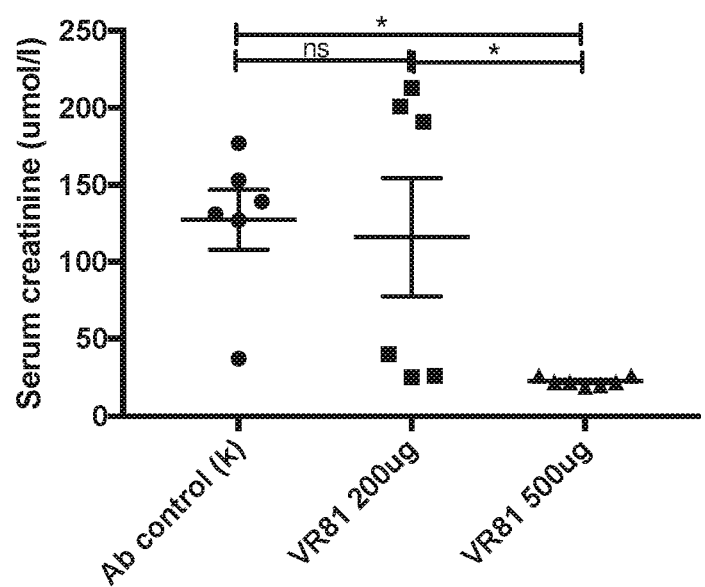
FIG. 12 is a graphical representation of serum creatinine concentrations in the warm renal IRI model (mean±SEM). Treatment of mice with 500 μg anti-G-CSFR antibody (VR81) significantly reduced serum creatinine concentrations compared to treatment of mice with 500 μg of an isotype control antibody. One-Way ANOVA Kruskal-Wallis test, Dunn's Multiple Comparison Test *$p<0.05$ ($n=6$-$8$ mice per group).

There was a significant reduction in serum creatinine and serum urea levels in mice treated with 500 μg of VR81, but not mice treated with 200 μg of VR81, or 500 μg of the isotype control antibody as shown in Table 5 and FIGS. 11 and 12.

TABLE 5

Serum creatinine and serum urea levels in mice dosed with 200 μg and 500 μg VR81/mouse. D'Agostino & Pearson omnibus normality test. One-Way ANOVA Kruskal-Wallis test, Dunn's Multiple Comparison Test for VR81 vs Ab control (*p < 0.05, **p < 0.01).

|  | Creatinine (UM) | Urea (mg/dL) |
|---|---|---|
| Control (500 μg) | 127.3 ± 19.5 | 507.7 ± 75.2 |
| VR81 (200 μg) | 116.0 ± 38.5 | 344 ± 94.2 |
| VR81 (500 μg) | 22.4 ± 1.0* | 84.42 ± 3.27** |

Example 8: Inhibition of G-CSF Signaling Reduces Complement C5 Activation and C5b-9 Deposition in a Warm Renal IRI Model To assess the effect of administration of anti-G-CSFR antibody (VR81) to mice subjected to warm renal ischemia-reperfusion injury (IRI), complement C5 activation was measured by analyzing C5a in plasma using a mouse C5a ELISA kit and C5b-9 deposition was measured by immunofluorescence staining of kidney sections according to Example 1.

Figure 14A:
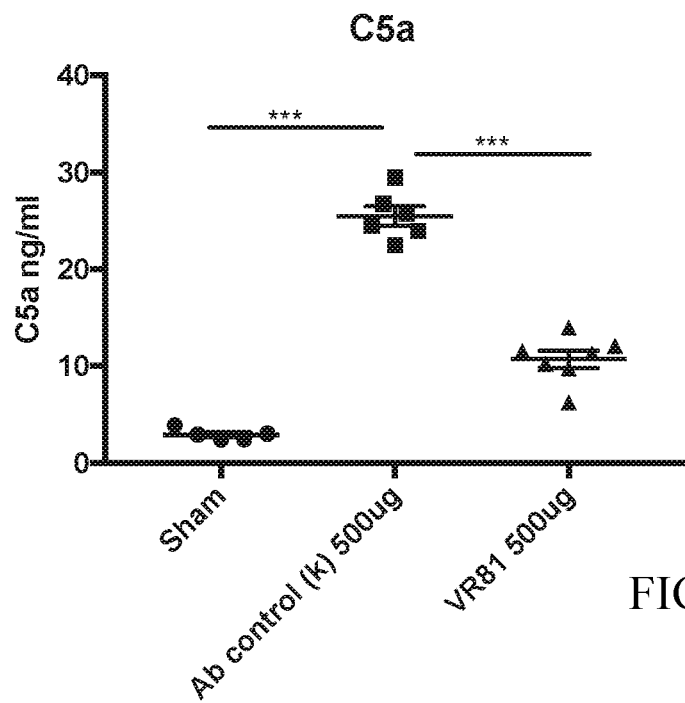
FIG. 14 is a graphical representation of plasma C5a (A) and kidney C5b-9 deposition (B).

There was a significant reduction in plasma C5a levels in mice treated with 500 μg of VR81, compared to mice treated with 500 μg of the isotype control antibody as shown in Table 6 and FIG. 14A.

Figure 14B:
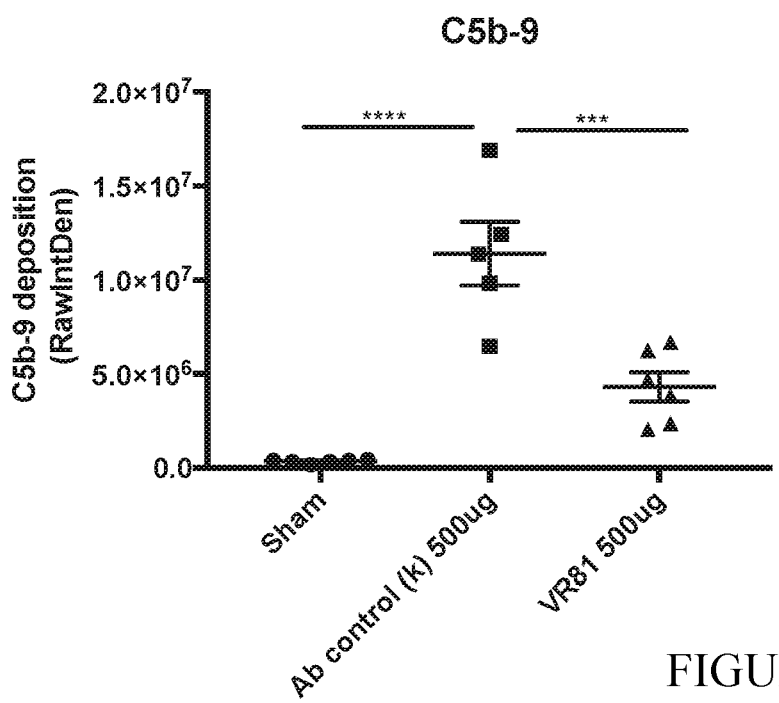

There was also a significant reduction in C5b-9 deposition in the kidneys of mice treated with 500 μg of VR81, compared to mice treated with 500 μg of the isotype control antibody as shown in Table 6 and FIG. 14B.

TABLE 6

Complement C5 activation and C5b-9 deposition in mice treated with 200 μg, or 500 μg VR81 ($*p < 0.05$, $p < 0.02$, $*p < 0.001$ versus Ab control).

| Treatment | C5a (ng/ml) | C5b-9 deposition (RawIntDen) |
|---|---|---|
| Sham | 2.93 ± 0.26 | 3.52 ± 0.38 × $10^5$ |
| Ab control (500 μg) | 25 ± 0.99 | 1.14 ± 0.17 × $10^7$ |
| VR81 (200 μg) | 17.31 ± 1.95 | 7.73 ± 1.6 × $10^6$ |
| VR81 (500 μg) | 10.69 ± 0.90 | 4.31 ± 0.78 × $10^6$ |

Example 9: Administration of an Inhibitor of G-CSF Signaling 1 h Before Ischemia Reduces Frequency of Neutrophils in Kidney and Blood in a Warm Renal IRI Model To assess the effect of administration of anti-G-CSFR antibody (VR81) to mice 1 h prior to ischemia in the warm renal IRI model, frequency of neutrophils (CD11b+Gr1+Ly6G+) in kidney and blood were measured by tissue digestion and flow cytometry according to the methods described in Example 1. 500 μg/mouse of the anti-C5 antibody, BB5.1, was used for comparison.

Figure 15:
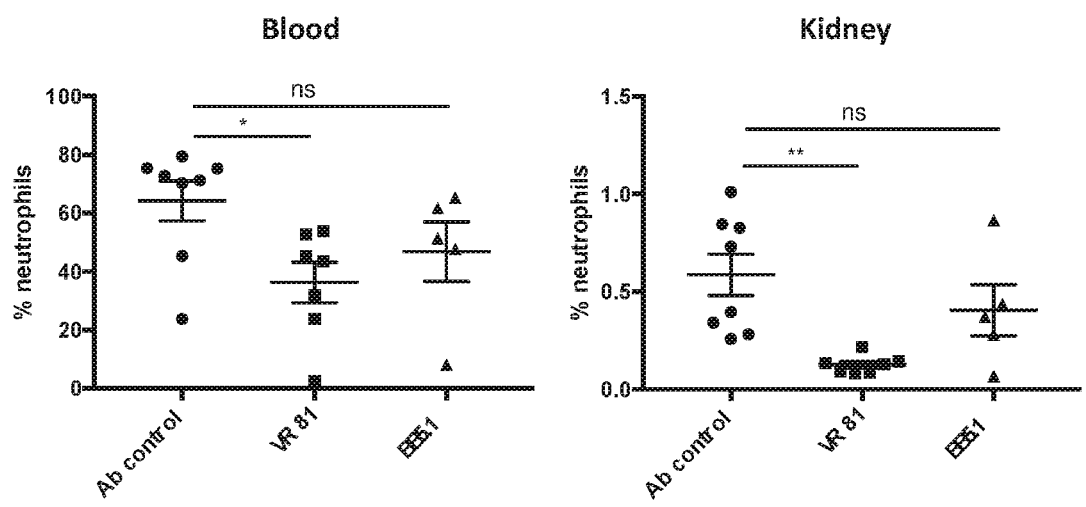
FIG. 15 is a graphical representation of the frequency of neutrophils (CD11b+Gr1+Ly6G+) in blood and kidney in the warm renal IRI model. Treatment with 500 µg/mouse of the anti-G-CSFR antibody VR81 1 h before ischemia significantly reduced the frequency of neutrophils in the kidney compared to treatment with an isotype control antibody. Treatment with 500 µg/mouse of control antibody BB5.1 did not significantly reduced the frequency of neutrophils in the kidney compared to treatment with an isotype control antibody. Stats: One-Way ANOVA Kruskal-Wallis test, Dunn's Multiple Comparison Test, *p<0.05, **p<0.01 (n=5-8 mice per group).

Treatment with 500 μg/mouse of the anti-G-CSFR antibody VR81 1 h before ischemia significantly reduced the frequency of neutrophils in blood and in the kidney compared to treatment with an isotype control antibody (FIG. 15). Treatment with 500 μg/mouse of control antibody BB5.1 did not significantly reduced the frequency of neutrophils in the kidney compared to treatment with an isotype control antibody. These results demonstrate that treatment with an inhibitor of G-CSF signaling 1 h before ischemia, while not as effective as treating 24 h before ischemia (FIG. 13), is sufficient to significantly reduce neutrophil numbers in blood and in the kidney.

The invention claimed is:

1. A method for reducing or hindering development of ischemia-reperfusion injury in a subject, the method comprising administering a compound that inhibits granulocyte colony stimulating factor (G-CSF) signaling, wherein the ischemia-reperfusion injury is due to or associated with tissue or organ transplantation, wherein the tissue or organ transplantation is a kidney transplantation and wherein the compound that inhibits G-CSF signaling is an antibody that specifically binds to G-CSF receptor (G-CSFR) and neutralizes G-CSF signaling, wherein the compound that inhibits G-CSF signaling is administered in an amount sufficient to have one or more of the following effects 24 hours after reperfusion:
  (i) reduce or prevent an increase in serum or plasma creatinine levels;
  (ii) reduce or prevent an increase in serum or plasma urea levels;
  (iii) reduce or prevent neutrophil infiltration;
  (iv) reduce or prevent macrophage infiltration;
  (v) reduce or prevent complement C5 activation; and
  (vi) reduce or prevent C5b-9 deposition.

2. The method of claim 1, wherein the compound that inhibits G-CSF signaling is administered between 0 and 48 hours before ischemia or reperfusion.

3. The method of claim 2, wherein the compound that inhibits G-CSF signaling is administered about 24 hours before ischemia or reperfusion.

4. The method of claim 2, wherein the compound that inhibits G-CSF signaling is administered in an amount sufficient to reduce or inhibit expression of one or more of the following 24 hours after reperfusion:

(i) kidney injury molecule 1 (KIM-1);
(ii) neutrophil gelatinase-associated lipocalin (NGAL);
(iii) interleukin 1 beta (IL-1β);
(iv) interleukin 6 (IL-6);
(v) tumor necrosis factor alpha (TNFα);
(vi) complement component 5a receptor 1 (C5AR1);
(vii) macrophage inflammatory protein 2-alpha (MIP2-alpha);
(viii) intercellular Adhesion Molecule 1 (ICAM-1);
(ix) E-selectin;
(x) C-X-C motif chemokine ligand 1 (CXCL1);
(xi) interleukin 8 receptor beta (IL-8Rβ); and
(xii) monocyte chemoattractant protein 1 (MCP-1).

5. The method of claim 1, wherein the compound that inhibits G-CSF signaling is administered to the subject, wherein the subject is a tissue or organ transplantation recipient.

6. The method of claim 1, wherein the compound that inhibits G-CSF signaling is administered to a tissue or organ transplantation donor prior to organ collection and/or to a tissue or organ prior to transplantation.

7. The method of claim 1, wherein the compound that inhibits G-CSF signaling is administered to:
  a) a tissue or organ transplant recipient prior to or at the time of transplanting the tissue or organ and then transplanting the tissue or organ into the tissue or organ transplant recipient;
  b) a tissue or organ transplant donor prior to collection of the tissue or organ; collecting the tissue or organ and transplanting the tissue or organ into a tissue or organ transplant recipient; or
  c) a harvested tissue or organ ex vivo and transplanting the harvested tissue or organ into a tissue or organ transplant recipient.

8. The method of claim 7, wherein the compound is administered to the subject prior to or during transplantation and then one or more additional doses is administered to the recipient following transplantation.

9. The method of claim 1, wherein the antibody comprises a VH comprising three complementarity determining regions (CDRs) of a VH comprising the amino acid sequence set forth in SEQ ID NO: 4 and a VL comprising three CDRs of a VL comprising the amino acid sequence set forth in SEQ ID NO: 5.

10. The method of claim 1, wherein the antibody comprises a heavy chain variable region (VH) comprising the amino acid sequence set forth in SEQ ID NO: 4 and a light chain variable region (VL) comprising the amino acid sequence set forth in SEQ ID NO: 5.

11. The method of claim 1, wherein the antibody comprises a VH comprising the amino acid sequence set forth in SEQ ID NO: 2 and a VL comprising the amino acid sequence set forth in SEQ ID NO: 3.

* * * * *

```
                          SEQUENCE LISTING

Sequence total quantity: 18
SEQ ID NO: 1             moltype = AA  length = 319
FEATURE                  Location/Qualifiers
REGION                   1..319
                         note = amino acids 25-335 of Homo sapiens G-CSFR (hG-CSFR)
                          with aC-terminal polyhistidine tag
source                   1..319
                         mol_type = protein
                         organism = synthetic construct
SEQUENCE: 1
ECGHISVSAP IVHLGDPITA SCIIKQNCSH LDPEPQILWR LGAELQPGGR QQRLSDGTQE   60
SIITLPHLNH TQAFLSCALN WGNSLQILDQ VELRAGYPPA IPHNLSCLMN LTTSSLICQW  120
EPGPETHLPT SFTLKSFKSR GNCQTQGDSI LDCVPKDGQS HCSIPRKHLL LYQNMGIWVQ  180
AENALGTSMS PQLCLDPMDV VKLEPPMLRT MDPSPEAAPP QAGCLQLSWE PWQPGLHINQ  240
KCELRHKPQR GEASWALVGP LPLEALQYEL CGLLPATAYT LQIRCIRWPL PGHWSDWSPS  300
LELRTTERAP THHHHHHHH                                               319

SEQ ID NO: 2             moltype = AA  length = 118
FEATURE                  Location/Qualifiers
REGION                   1..118
                         note = VH of C1.2
source                   1..118
                         mol_type = protein
                         organism = synthetic construct
SEQUENCE: 2
EVQLLESGGG LVQPGGSLRL SCAASGFTFS LYWMGWVRQA PGKGLEWVSS ISSSGGVTPY   60
ADSVKGRFTI SRDNSKNTLY LQMNSLRAED TAVYYCAMLG ELGWFDPWGQ GTLVTVSS    118

SEQ ID NO: 3             moltype = AA  length = 107
FEATURE                  Location/Qualifiers
REGION                   1..107
                         note = VL of C1.2
source                   1..107
                         mol_type = protein
                         organism = synthetic construct
SEQUENCE: 3
DIQMTQSPSA LSASVGDRVT ITCRASQGIS SYLNWYQQKP GKAPKLLIYY ASNLQNGIPS   60
RFSGSGSGTD FTLTISSLQP EDFATYHCQQ SYSTPLTFGG GTNVEIR                107

SEQ ID NO: 4             moltype = AA  length = 118
FEATURE                  Location/Qualifiers
REGION                   1..118
                         note = VH of C1.2G
```

```
                           source          1..118
                                           mol_type = protein
                                           organism = synthetic construct
SEQUENCE: 4
EVQLLESGGG LVQPGGSLRL SCAASGFTFS LYWMGWVRQA PGKGLEWVSS ISSSGGVTPY    60
ADSVKGRFTI SRDNSKNTLY LQMNSLRAED TAVYYCAKLG ELGWFDPWGQ GTLVTVSS    118

SEQ ID NO: 5               moltype = AA  length = 107
FEATURE                    Location/Qualifiers
REGION                     1..107
                           note = VLof C1.2G
source                     1..107
                           mol_type = protein
                           organism = synthetic construct
SEQUENCE: 5
DIQMTQSPSS LSASVGDRVT ITCRASQGIS SYLNWYQQKP GKAPKLLIYY ASNLQNGVPS    60
RFSGSGSGTD FTLTISSLQP EDFATYYCQQ SYSTPLTFGG GTKVEIK                 107

SEQ ID NO: 6               moltype = AA  length = 5
FEATURE                    Location/Qualifiers
REGION                     1..5
                           note = HCDR1 of C1.2
source                     1..5
                           mol_type = protein
                           organism = synthetic construct
SEQUENCE: 6
LYWMG                                                                 5

SEQ ID NO: 7               moltype = AA  length = 17
FEATURE                    Location/Qualifiers
REGION                     1..17
                           note = C1.2 HCDR2
source                     1..17
                           mol_type = protein
                           organism = synthetic construct
SEQUENCE: 7
SISSSGGVTP YADSVKG                                                   17

SEQ ID NO: 8               moltype = AA  length = 9
FEATURE                    Location/Qualifiers
REGION                     1..9
                           note = C1.2 HCDR3
source                     1..9
                           mol_type = protein
                           organism = synthetic construct
SEQUENCE: 8
LGELGWFDP                                                             9

SEQ ID NO: 9               moltype = AA  length = 11
FEATURE                    Location/Qualifiers
REGION                     1..11
                           note = C1.2 LCDR1
source                     1..11
                           mol_type = protein
                           organism = synthetic construct
SEQUENCE: 9
RASQGISSYL N                                                         11

SEQ ID NO: 10              moltype = AA  length = 6
FEATURE                    Location/Qualifiers
REGION                     1..6
                           note = C1.2 LCDR2
source                     1..6
                           mol_type = protein
                           organism = synthetic construct
SEQUENCE: 10
ASNLQN                                                                6

SEQ ID NO: 11              moltype = AA  length = 9
FEATURE                    Location/Qualifiers
REGION                     1..9
                           note = C1.2 LCDR3
source                     1..9
                           mol_type = protein
                           organism = synthetic construct
SEQUENCE: 11
QQSYSTPLT                                                             9

SEQ ID NO: 12              moltype = AA  length = 8
```

| FEATURE | Location/Qualifiers |
|---|---|
| REGION | 1..8 |
| | note = consensus sequence of HCDR3 of C1.2 |
| VARIANT | 5 |
| | note = X is an amino acid selected from the group consisting oftryptophan, glutamine, methionine, serine, phenylalanine,glutamic acid and histidine |
| VARIANT | 6 |
| | note = X iis an amino acid selected from the group consisting ofphenylalanine, tyrosine, methionine, serine, glycine andisoleucine |
| VARIANT | 7 |
| | note = X is an amino acid selected from the group consisting of asparticacid, methionine, glutamine, serine, leucine, valine, arginineand histidine |
| VARIANT | 8 |
| | note = X is an amino acid selected from the group consisting of prolinegltuamic acid, alanine, leucine, phenylalanine, tyronis,threonine, asparagine, aspartic acid, serine , glycine, arginine,lysine |
| source | 1..8 |
| | mol_type = protein |
| | organism = synthetic construct |

SEQUENCE: 12
LGELXXXX                                                                 8

SEQ ID NO: 13      moltype =    length =
SEQUENCE: 13
000

SEQ ID NO: 14      moltype = AA   length = 445
FEATURE            Location/Qualifiers
REGION             1..445
                   note = C1.2G heavy chain IgG4 with S241P mutation
source             1..445
                   mol_type = protein
                   organism = synthetic construct
SEQUENCE: 14
EVQLLESGGG LVQPGGSLRL SCAASGFTFS LYWMGWVRQA PGKGLEWVSS ISSSGGVTPY   60
ADSVKGRFTI SRDNSKNTLY LQMNSLRAED TAVYYCAKLG ELGWFDPWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLGK                                        445

SEQ ID NO: 15      moltype = AA   length = 214
FEATURE            Location/Qualifiers
REGION             1..214
                   note = C1.2G with kappa light chain
source             1..214
                   mol_type = protein
                   organism = synthetic construct
SEQUENCE: 15
DIQMTQSPSS LSASVGDRVT ITCRASQGIS SYLNWYQQKP GKAPKLLIYY ASNLQNGVPS   60
RFSGSGSGTD FTLTISSLQP EDFATYYCQQ SYSTPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 16      moltype = AA   length = 836
FEATURE            Location/Qualifiers
source             1..836
                   mol_type = protein
                   organism = Homo sapiens
SEQUENCE: 16
MARLGNCSLT WAALIILLLP GSLEECGHIS VSAPIVHLGD PITASCIIKQ NCSHLDPEPQ   60
ILWRLGAELQ PGGRQQRLSD GTQESIITLP HLNHTQAPLS CCLNWGNSLQ ILDQVELRAG  120
YPPAIPHNLS CLMNLTTSSL ICQWEPGPET HLPTSFTLKS FKSRGNCQTQ GDSILDCVPK  180
DGQSHCCIPR KHLLLYQNMG IWVQAENALG TSMSPQLCLD PMDVVKLEPP MLRTMDPSPE  240
AAPPQAGCLQ LCWEPWQPGL HINQKCELRH KPQRGEASWA LVGPLPLEAL QYELCGLLPA  300
TAYTLQIRCI RWLPLPGHWSD WSPSLELRTT ERAPTVRLDT WWRQRQLDPR TVQLFWKPVP  360
LEEDSGRIQG YVVSWRPSGQ AGAILPLCNT TELSCTFHLP SEAQEVALVA YNSAGTSRPT  420
PVVFSESRGP ALTRLHAMAR DPHSLWVGWE PPNPWPQGYV IEWGLGPPSA SNSNKTWRME  480
QNGRATGFLL KENIRPFQLY EIIVTPLYQD TMGPSQHVYA YSQEMAPSHA PELHLKHIGK  540
TWAQLEWVPE PPELGKSPLT HYTIFWTNAQ NQSFSAILNA SSRGFVLHGL EPASLYHIHL  600
MAASQAGATN STVLTLMTLT PEGSELHIIL GLFGLLLLLT CLCGTAWLCC SPNRKNPLWP  660
SVPDPAHSSL GSWVPTIMEE DAFQLPGLGT PPITKLTVLE EDEKKPVPWE SHNSSETCGL  720
PTLVQTYVLQ GDPRAVSTQP QSQSGTSDQV LYGQLLGSPT SPGPGHYLRC DSTQPLLAGL  780

```
TPSPKSYENL WFQASPLGTL VTPAPSQEDD CVFGPLLNFP LLQGIRVHGM EALGSF        836

SEQ ID NO: 17           moltype = AA  length = 319
FEATURE                 Location/Qualifiers
REGION                  1..319
                        note = Ig and CRH domains of Macaca fascicularis G-CSFR
                        (cynoG-CSFR)with a C-terminal polyhistidine tag
source                  1..319
                        mol_type = protein
                        organism = synthetic construct
SEQUENCE: 17
ECGHISVSAP IVHLGDPITA SCIIKQNCSH LDLEPQILWR LGAELQPGGR QQRLSDGSQQ    60
STITLPHLNH TRAFLSCALN WGNSLQILDQ VELRAGYPPA VPRNLSCLMN LTTSSLICQW   120
EPGPETHLPT SFTLKSFKSR GNCQTQGDSI MDCVPEDGQS HCSIPRRHLL LYQNMGIWVQ   180
AENALGTSMS PQLCLEPMDV VKLEPPMLRT MDPSPEAAPP QAGCLQLSWE PWQPALHINQ   240
KCELRHKPQS GEASWALVGP LPLEALRYEL CGLLPATAYT LQIRCIRWPL PGHWSNWSPS   300
LELRTTERAP THHHHHHHH                                                319

SEQ ID NO: 18           moltype = AA  length = 444
FEATURE                 Location/Qualifiers
REGION                  1..444
                        note = C1.2G heavy chain IgG4 with S241P mutation and
                        lacking C-terminallysine residue
source                  1..444
                        mol_type = protein
                        organism = synthetic construct
SEQUENCE: 18
EVQLLESGGG LVQPGGSLRL SCAASGFTFS LYWMGWVRQA PGKGLEWVSS ISSSGGVTPY    60
ADSVKGRFTI SRDNSKNTLY LQMNSLRAED TAVYYCAKLG ELGWFDPWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                          444
```